(12) United States Patent
Katsumi et al.

(10) Patent No.: US 8,834,791 B2
(45) Date of Patent: Sep. 16, 2014

(54) SAMPLE ANALYZER AND NON-TRANSITORY STORAGE MEDIUM

(75) Inventors: Hironori Katsumi, Kobe (JP); Kazuya Fukuda, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 13/046,059

(22) Filed: Mar. 11, 2011

(65) Prior Publication Data

US 2011/0223063 A1 Sep. 15, 2011

(30) Foreign Application Priority Data

Mar. 12, 2010 (JP) ................. 2010-055941

(51) Int. Cl.
*G01N 33/48* (2006.01)
(52) U.S. Cl.
CPC .... *G11N 35/1002* (2013.01); *G11N 2035/0443* (2013.01); *G11N 2035/00435* (2013.01); *G11N 2035/0455* (2013.01); *G11N 2035/00386* (2013.01); *G11N 2035/0451* (2013.01)
USPC .................. 422/64; 422/63; 436/45
(58) Field of Classification Search
CPC .................. G01N 35/1002; G01N 2035/0455; G01N 2035/00386; G01N 2035/0443; G01N 2035/0451
See application file for complete search history.

(56) References Cited

U.S. PATENT DOCUMENTS

| 2,682,452 | A | * | 6/1954 | Wainwright | 422/256 |
| 4,984,628 | A | * | 1/1991 | Uchida et al. | 165/256 |
| 2009/0004057 | A1 | * | 1/2009 | Sato | 422/63 |
| 2011/0232769 | A1 | * | 9/2011 | Nichogi et al. | 137/3 |

FOREIGN PATENT DOCUMENTS

| JP | 60-116188 U | | 8/1985 |
| JP | 02-089359 U | | 7/1990 |
| JP | 02-184345 A | | 7/1990 |
| JP | 2008-122421 A | | 5/2008 |
| JP | 2009-80034 | * | 4/2009 |
| JP | 2009-139269 | * | 6/2009 |
| WO | WO 2010-021172 | * | 2/2010 |

* cited by examiner

*Primary Examiner* — P. Kathryn Wright
(74) *Attorney, Agent, or Firm* — Brinks Gilson & Lione

(57) ABSTRACT

The present invention is a sample analyzer comprising: a reagent storage configured to store a reagent container containing a reagent used for analyzing a sample, wherein the reagent storage comprises a liquid storing section which stores a liquid such that a surface of the liquid contacts an air within the reagent storage; and a liquid supply unit configured to supply the liquid into the liquid storing section.

18 Claims, 17 Drawing Sheets

SAMPLE ANALYZER AND NON-TRANSITORY STORAGE MEDIUM

RELATED APPLICATIONS

This application claims priority under 35 U.S.C. §119 to Japanese Patent Application No. 2010-055941 filed on Mar. 12, 2010, the entire content of which is hereby incorporated by reference.

FIELD OF THE INVENTION

The present invention relates to a sample analyzer for analyzing a sample using a reagent accommodated in a reagent container, and a non-transitory storage medium.

BACKGROUND

An analyzer for analyzing a measurement result of a measurement sample prepared by mixing a sample and a reagent is conventionally known. In such an analyzer, the reagent is accommodated in a reagent container and stored in a predetermined reagent storage, and is stored cool in the reagent storage at a predetermined temperature to prevent degradation.

U.S. Patent Publication No. 2009/004057 discloses an automatic analyzer including a reagent storage having a function of cooling a reagent. The reagent storage of the automatic analyzer includes a reagent case with a bottom wall and a peripheral wall, a reagent cover for blocking an upper opening of the reagent case, a reagent table arranged within the reagent case and mounted with a rack holding a plurality of reagent containers, a cooling unit for cooling air within the reagent case, and a fan for circulating the air within the reagent case.

The automatic analyzer is configured to cool the reagent in the reagent storage by circulating the air cooled by the cooling unit with the fan.

In such an automatic analyzer, the reagent may evaporate from the opening of the reagent container stored in the reagent storage. When the reagent evaporates, the component concentration changes, thereby possibly adversely affecting the analysis result of the sample.

In the automatic analyzer described in U.S. Patent Publication No. 2009/004057, a devisal is made on the structure of the reagent case and the shape of the rack for holding the reagent, thereby controlling the flow of air within the reagent storage and suppressing the air flow near the opening of the reagent container to prevent the evaporation of the reagent. However, it is difficult to sufficiently suppress the evaporation of the reagent by simply controlling the flow of air within the reagent storage.

SUMMARY OF THE INVENTION

The scope of the present invention is defined solely by the appended claims, and is not affected to any degree by the statements within this summary.

A first aspect of the present invention is a sample analyzer comprising: a reagent storage configured to store a reagent container containing a reagent used for analyzing a sample, wherein the reagent storage comprises a liquid storing section which stores a liquid such that a surface of the liquid contacts an air within the reagent storage; and a liquid supply unit configured to supply the liquid into the liquid storing section.

A second aspect of the present invention is at least one non-transitory storage medium which stores programs executable collectively by at least one processor to: supply a liquid into a liquid storing section within a reagent storage which is configured to store a reagent container containing a reagent used for analyzing a sample; and store the liquid supplied into the liquid storing section such that a surface of the liquid contacts an air within the reagent storage.

DETAILED DESCRIPTION OF THE EMBODIMENT

Figure 1:
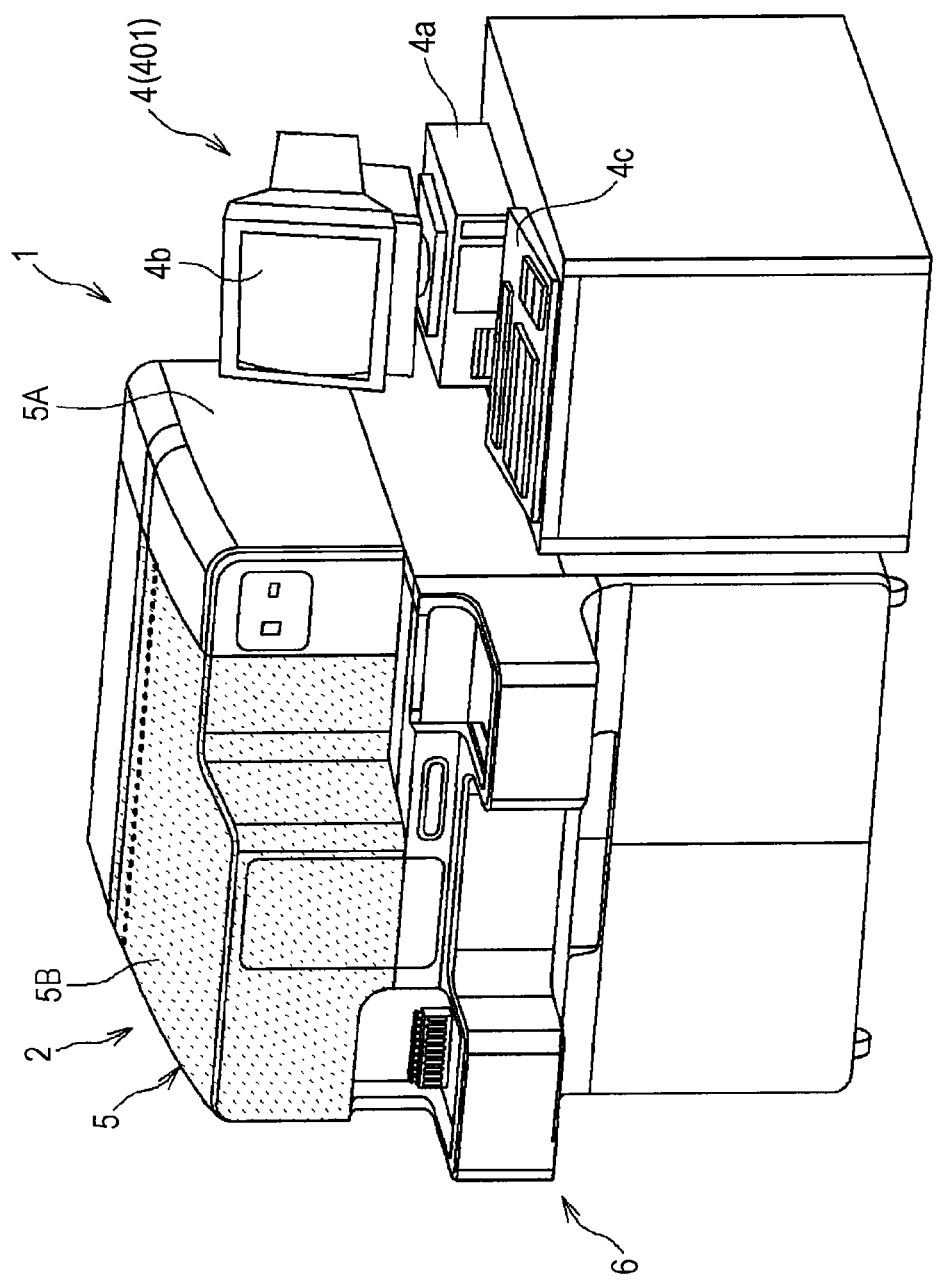
FIG. 1 is a perspective view showing an overall configuration of a sample analyzer according to an embodiment of the present invention.

The embodiments of the sample analyzer of the present invention will be described in detail below with reference to the accompanied drawings. FIG. 1 is a perspective view showing an overall configuration of a sample analyzer 1 according to the embodiment of the present invention, and FIG. 2 is a plan view showing the schematic configuration of a measurement device.

A sample analyzer 1 is an apparatus for analyzing the amount or degree of activity of a specific substance related to coagulation and fibrolytic function of the blood by optically measuring the same, and uses blood plasma for the sample. In the sample analyzer 1 according to the present embodiment, the optical measurement of the sample is carried out using a coagulation time method, a synthetic substrate method, and an immune nephelometry. The coagulation time method used in the present embodiment is a measurement method for detecting the process in which the sample coagulates as change in transmitted light. The measurement item includes PT (prothrombin time), APTT (activated partial thromboplastin time) and Fbg (fibrinogen amount). The measurement item of the synthetic substrate method includes AT III and the like, and the measurement method of the immune nephelometry includes D dimer, FDP, and the like.

Figure 2:
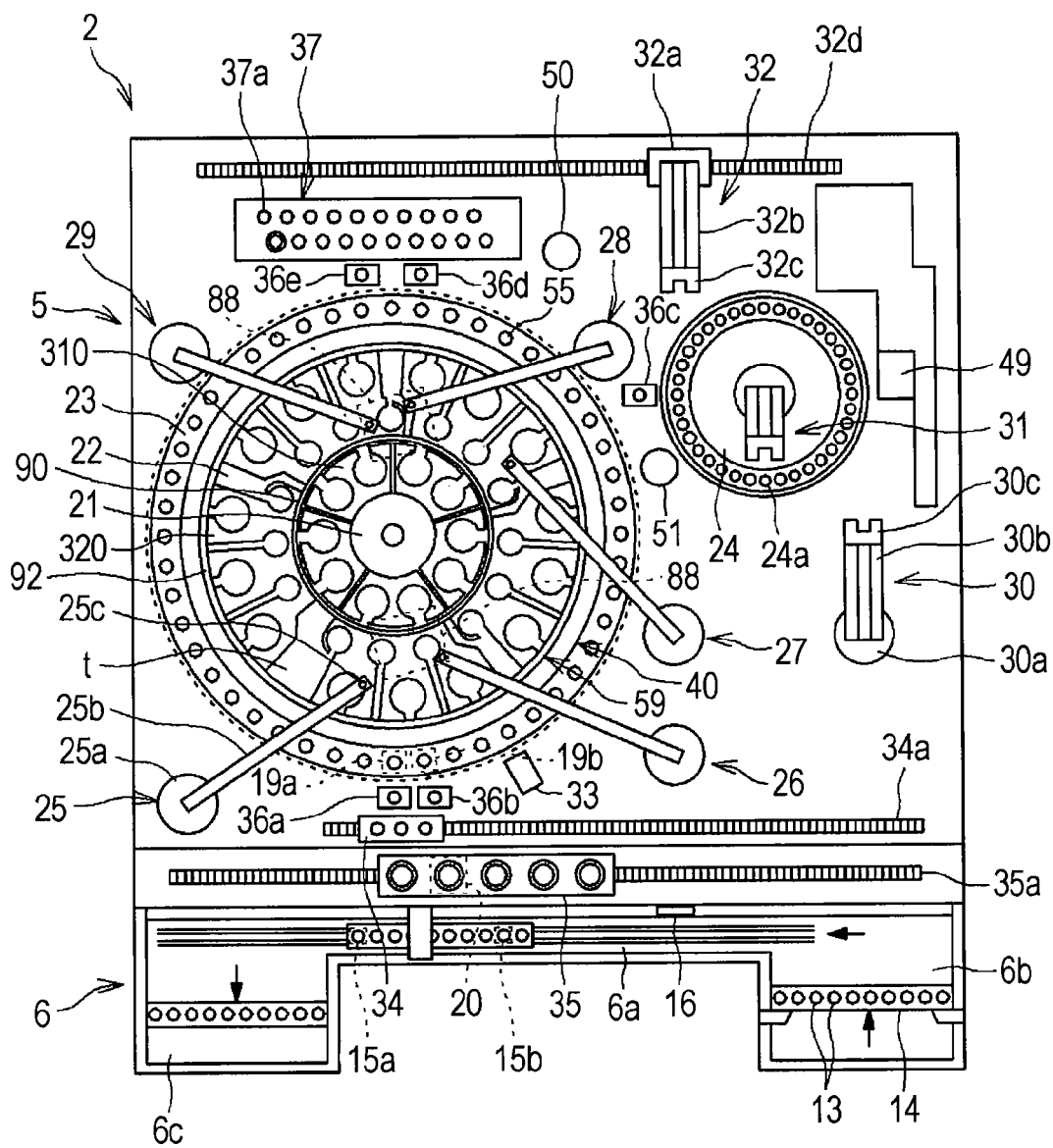
FIG. 2 is a plan view showing the schematic configuration of a measurement device of the sample analyzer shown in FIG. 1.

As shown in FIG. 1 and FIG. 2, the sample analyzer 1 is configured by a measurement device 2, and a control device 4 electrically connected to the measurement device 2. The measurement device 2 is configured by a measurement mechanism section 5 and a transport mechanism section 6 arranged on the front surface side of the measurement mechanism section 5, where the measurement mechanism section 5 is covered by a housing 5A and a cover body 5B. The cover body 5B is attached in an openable/closable manner at the left side in the upper front part of the housing 5A. The front side of the measurement mechanism section 5 can be exposed to the outside by opening the cover body 5B.

[Configuration of Transport Mechanism Section]

As shown in FIG. 2, the transport mechanism section 6 has a function of transporting a sample rack 14 holding a plurality of sample containers (test tubes) 13 accommodating the sample in the left and right direction on a transport path 6a and positioning the sample container 13 at predetermined sample aspirating positions 15a, 15b to supply the sample to the measurement mechanism section 5. The transport mechanism section 6 includes a rack set region 6b for setting the sample rack 14 in which the sample container 13 accommodating the non-processed sample is stored, and a rack accommodating region 6c for accommodating the sample rack 14 in which the sample container 13 accommodating the processed sample is stored at both ends of the transport path 6a. The transport mechanism section 6 includes a sample barcode reader 16 for reading the barcode attached to the sample container 13.

[Configuration of Measurement Mechanism Section]

The measurement mechanism section 5 is configured to perform optical measurement on the sample supplied from the transport mechanism section 6 to obtain optical information about the supplied sample. In the present embodiment, the optical measurement is performed on the sample dispensed into the cuvette of the measurement mechanism section 5 from the sample container 13 mounted on the sample rack 14 of the transport mechanism section 6.

The measurement mechanism section 5 includes a first reagent table 21, a second reagent table 22, a cuvette table 23, a warming table 24, a first sample dispensing unit 25, a second sample dispensing unit 26, a first reagent dispensing unit 27, a second reagent dispensing unit 28, a third reagent dispensing unit 29, a first catcher unit 30, a second catcher unit 31, a third catcher unit 32, a reagent barcode reader 33, a cuvette transport unit 34, a diluted solution transport unit 35, pipette cleaners 36a to 36e, a detection unit 37, and the like.

The first reagent table 21, the second reagent table 22, the cuvette table 23, and the warming table 24 are circular tables, and are rotation driven independently both in the clockwise direction and in the counterclockwise direction by a drive unit such as a stepping motor.

The first reagent table 21 and the second reagent table 22 are arranged in a reagent storage 40 (reagent cold storage unit), and a first reagent container rack 310 and a second reagent container rack 320 that hold a reagent container 300 accommodating the reagent are set on the first reagent table 21 and the second reagent table 22. Various types of reagents for causing coagulation reaction of the blood plasma are accommodated in the reagent container 300. The details of the reagent storage 40 will be described later.

The first sample dispensing unit 25 includes a supporting portion 25a, an arm 25b which basal end side is supported by the supporting portion 25a, and a dispensing portion 25c arranged at the distal end of the arm 25b. The arm 25b is rotatably driven in the horizontal direction with the basal end as a supporting point and is up/down driven in the up and down direction by the drive unit such as the stepping motor. The dispensing portion 25c is attached with a pipette, and the sample and the like are aspirated and discharged using the pipette.

The second sample dispensing unit 26, and the first to third reagent dispensing units (reagent aspirating units) 27 to 29 also have a configuration similar to the first sample dispensing unit 25. In other words, the units 27 to 29 each include a supporting portion, an arm, and a dispensing portion, which arm is rotatably driven and up/down driven by the drive unit. The dispensing portion is attached with a pipette, and the sample and the reagent are aspirated and discharged using the pipette.

The first catcher unit 30 includes a supporting portion 30a, an extendable arm 30b supported by the supporting portion 30a, and a gripping portion 30c arranged at the distal end of the arm 30b. The arm 30b is rotatably driven by the drive unit such as the stepping motor, and the gripping portion 30c grips the cuvette. The second catcher unit 31 also has a configuration similar to the first catcher unit 30, and is driven by the drive unit such as the stepping motor.

The third catcher unit 32 includes a supporting portion 32a, an extendable arm 32b supported by the supporting portion 30a, and a gripping portion 32c at the distal end of the arm 32b. The supporting portion 32a is driven along a rail 32d arranged in the left and right direction. The gripping portion 32c can grip the cuvette.

The reagent barcode reader 33 reads the barcode attached to the reagent container 300 stored in the reagent storage 40 and the reagent container racks 310, 320 for holding the reagent container 300. The reagent barcode reader 33 is arranged on the outer side of the reagent storage 40, and can read the barcode of the reagent storage 40 through a slit 46 (see FIG. 6) formed in the reagent storage 40 and opened and closed by a shutter.

The cuvette transport unit 34 and the diluted solution transport unit 35 each drive the rails 34a, 35a in the left and right direction. The cuvette transport unit 34 and the diluted solution transport unit 35 are each formed with a holding hole for holding the cuvette and the diluted solution container.

The measurement mechanism section 5 includes a cuvette port 49 and discarding ports 50, 51. The cuvette port 49 is constantly supplied with new cuvettes. The new cuvette is set in the holding hole of the cuvette transport unit 34 and the holding hole of the cuvette table 23 by the first catcher unit 30 and the second catcher unit 31. The discarding ports 50, 51 are holes for discarding the cuvettes that are finished with the analysis and are no longer necessary. A cuvette discarding unit 52 (see FIG. 14) for storing discarded cuvettes is arranged in the housing 5A of the sample analyzer 1.

The pipette cleaners 36a to 36e are each used to clean the pipettes of the first and second sample dispensing units 25, 26, and the first to third reagent dispensing units 27 to 29. The pipette cleaners 36a to 36e are formed with a hole, to which the pipette is inserted, in the up and down direction, and cleans the outer surface of the pipette with a cleaning solution supplied to the hole.

The detection unit 37 has a plurality of (20 in the illustrated example) holding holes 37a for accommodating the cuvette formed at the upper surface, and a detecting portion (not shown) arranged on the back side at the lower surface. When the cuvette is set in the holding hole 37a, the optical information reflecting the component contained in the measurement specimen in the cuvette is detected by the detecting portion.

Figure 3:
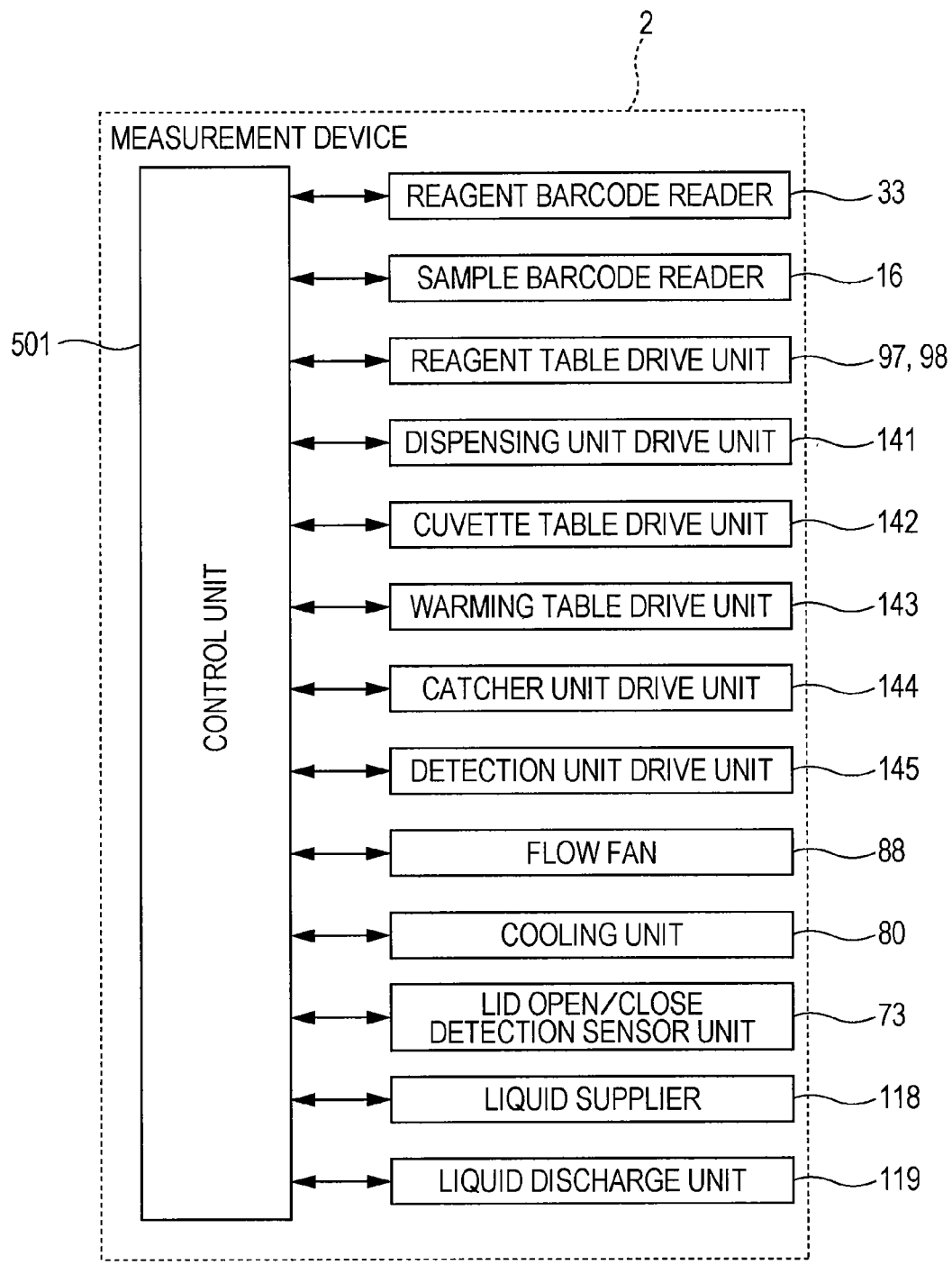
FIG. 3 is a block diagram showing a configuration of a measurement device.
Figure 4:
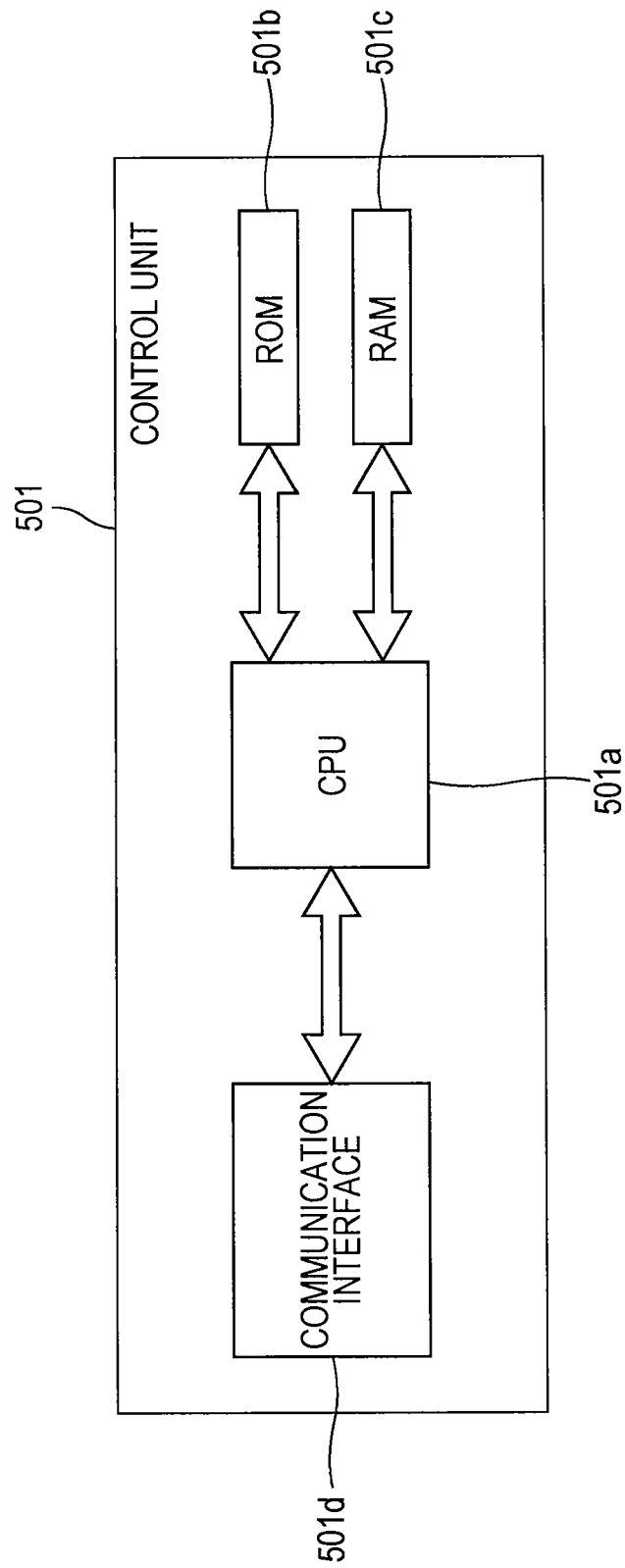
FIG. 4 is a block diagram showing a configuration of a control unit of the measurement device.

FIG. 3 is a block diagram showing a configuration of the measurement device of the sample analyzer 1, and FIG. 4 is a block diagram showing a configuration of a control unit of the measurement device. As shown in FIG. 3, each drive unit 97, 98, 141 to 145 of the first and second reagent tables 21, 22, the cuvette table 23, the warming table 24, the first and second sample dispensing units 25, 26, the first to third reagent dispensing units 27 to 29, the first to third catcher units 30 to 32, the cuvette transport unit 34, the diluted solution transport unit 35, the pipette cleaners 36a to 36e, and the detection unit 37, the reagent barcode reader 33, the sample barcode reader 16, and the like are electrically connected to a control unit 501 of the measurement device 2, and operation controlled by the control unit 501. The detection unit 37 is configured to transmit the acquired optical information to the control unit 501.

As shown in FIG. 4, the control unit 501 is mainly configured by a CPU 501a, a ROM 501b, a RAM 501c, and a communication interface 501d. The CPU 501a can execute computer programs stored in the ROM 501b and the computer programs read by the RAM 501c. The ROM 501b stores computer programs to be executed by the CPU 501a, data used for executing the computer program, and the like. The RAM 501c is used to read out the computer programs recorded on the ROM 501b, and is used as a work region of the CPU 501a when executing the computer program.

The communication interface 501d is connected to the control device 4, and has a function of transmitting optical information of the sample to the control device 4 and receiving the signal from the control unit 4a of the control device 4. The communication interface 501d has a function of transmitting a command from the CPU 501a for driving each unit of the transport mechanism section 6 and the measurement mechanism section 5.

[Configuration of Control Device]

The control device 4 includes a personal computer 401 (PC), as shown in FIG. 1, and includes the control unit 4a, a display unit 4b, and a keyboard 4c for inputting information. The control unit 4a has a function of transmitting an operation start signal of the measurement mechanism section 5 to the control unit 501 of the measurement mechanism section 5 and analyzing the optical information of the sample obtained in the measurement mechanism section 5. The display 4b is arranged to display information regarding the interference substance (hemoglobin, chyle (lipid), and bilirubin) in the sample and the analysis result obtained in the control unit 4a.

Figure 5:
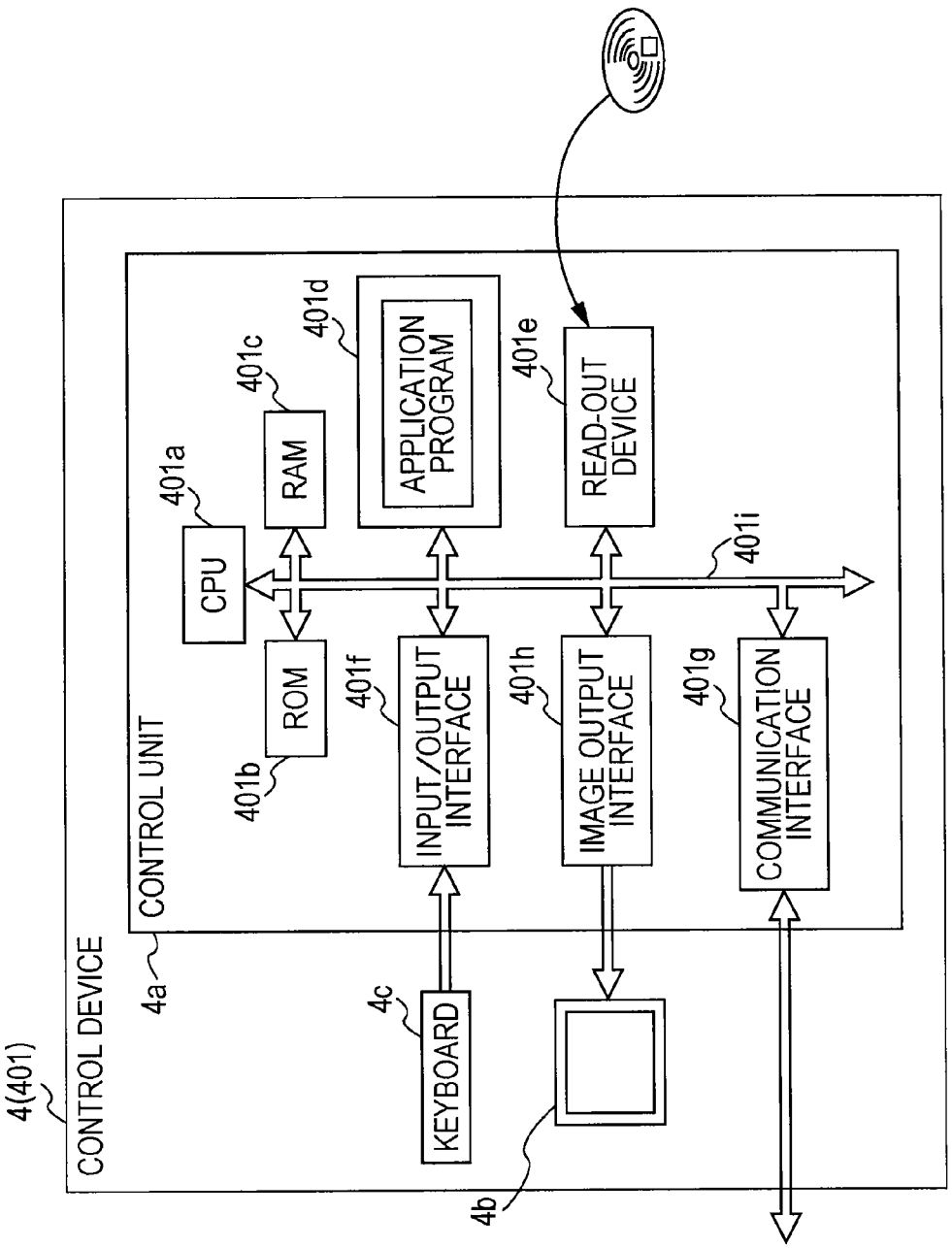
FIG. 5 is a block diagram showing a configuration of the control device of the sample analyzer shown in FIG. 1.

FIG. 5 is a block diagram showing a configuration of the control device. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

[Outline of Operation of Measurement Device]

The outline of the operation in the measurement device 2 will now be described. First, as shown in FIG. 2, when the sample rack 14 accommodating the sample container 13 is set in the rack set region 6b of the transport mechanism section 6, the relevant sample rack 14 is sent up to the back end (upper side in the figure) in the rack set region 6b, and then transported in the leftward direction on the transport path 6a. The barcode label attached to the sample container 13 is then read by the sample barcode reader 16, and then the sample container 13 is positioned at the predetermined sample aspirating position 15a. The sample rack 14, which aspiration of the sample is all finished, is transported to the rack accommodating region 6c.

The first sample dispensing unit 25 aspirates the sample from the sample container 13 positioned at the predetermined sample aspirating position 15a by the transport mechanism section 6. The sample aspirated by the first sample dispensing unit 25 is discharged to the cuvette set in the cuvette holding hole 55 positioned at a sample discharging position 19a at the front part of the cuvette table 23.

The second sample dispensing unit 26 aspirates the sample accommodated in the cuvette set in the cuvette holding hole 55 at a sample aspirating position 19b at the front part of the cuvette table 23, or the sample of the sample container 13 positioned at the predetermined sample aspirating position 15b by the transport mechanism section 6. The sample aspirated by the second sample dispensing unit 26 is discharged to the cuvette set in the cuvette transport unit 34. The second sample dispensing unit 26 can aspirate the diluted solution set in the diluted solution transport unit 35. In this case, the second sample dispensing unit 26 aspirates the sample at the sample aspirating position 15b after aspirating the diluted solution at the diluted solution aspirating position 20 before aspirating the sample.

After the dispensing task is finished, the first sample dispensing unit 25 and the second sample dispensing unit 26 have the pipettes inserted to the holes of the pipette cleaners 36a, 36b to be cleaned with the cleaning solution supplied to the hole.

The cuvette transport unit 34 is driven in the rightward direction on the rail 34a at a predetermined timing when the sample is discharged into the accommodated cuvette. The cuvette accommodating the sample set in the cuvette transport unit 34 is then gripped by the first catcher unit 30, and set in the cuvette holding hole 24a of the warming table 24.

The second catcher unit 31 then grips the cuvette accommodating the sample set in the holding hole 24a and moves it to immediately above the pipette cleaner 36c. The first reagent dispensing unit 27 aspirates the reagent in the predetermined reagent container 300 arranged at the first reagent table 21 or the second reagent table 22, and discharges the reagent to the cuvette gripped by the second catcher unit 31. The second catcher unit 31 stirs the cuvette discharged with the reagent, and sets the cuvette in the cuvette holding hole 24a of the warming table 24.

The cuvette held at the cuvette holding hole 24a of the warming table 24 is gripped by the third catcher unit 32, and is positioned in a region immediately above the pipette cleaner 36d or a region immediately above the pipette cleaner 36e. The second reagent dispensing unit 28 and the third reagent dispensing unit 29 aspirate the reagent from the reagent container 300 arranged at the first reagent table 21 or the second reagent table 22, and discharges the reagent to the cuvette gripped by the third catcher unit 32. The third catcher unit 32 sets the cuvette discharged with the reagent in the holding hole 37a of the detection unit 37. Thereafter, the optical information is detected from the measurement specimen accommodated in the cuvette in the detection unit 37.

After the dispensing task is finished, the first to third reagent dispensing units 27 to 29 have the pipettes inserted to the holes of the pipette cleaners 36c to 36e and cleaned for every dispersion of different reagents.

The cuvettes that are finished with the detection by the detection unit 37 and are no longer necessary are gripped by the third catcher unit 32, and discarded to the discarding port 50. When the analysis is finished and is no longer necessary, the cuvette held in the cuvette holding hole 55 of the cuvette table 23 is also positioned in the location near the second catcher unit 31 by the rotation of the cuvette table 23. The second catcher unit 31 grips the cuvette that is no longer necessary held at the cuvette holding hole 55, and discards it to the discarding port 51.

[Configuration of Reagent Storage and Cooling Function]

The reagent storage 40 is provided to chill store the reagent container 300 accommodating the reagent to be added to the sample in the cuvette at low temperature (about 10° C.) and to transport the same in the rotating direction. The reagent is suppressed from being altered by being stored at low temperature. The reagent container 300 accommodating the reagent is arranged in the reagent storage 40, and the reagent arrangement section 59 for performing the rotation transport is also arranged.

Figure 6:
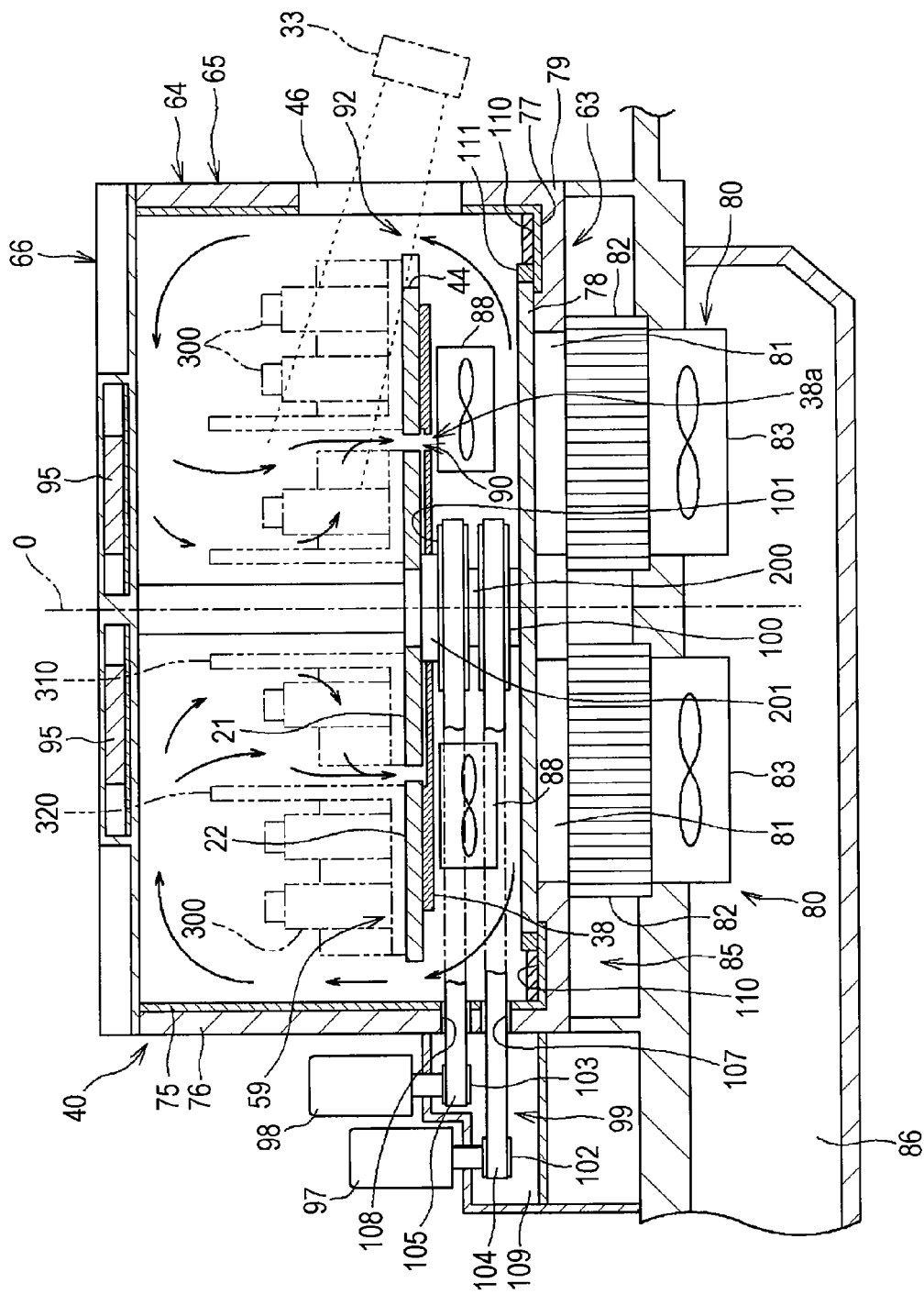
FIG. 6 is a cross-sectional view schematically showing a reagent storage shown in FIG. 1.

FIG. 6 is a side cross-sectional view schematically showing the reagent storage 40. The reagent arrangement section 59 includes a first reagent table (first arrangement section) 21 of circular shape and a second reagent table (second arrangement section) 22 of circular ring shape arranged concentrically with respect to the first reagent table 21 on the radially outward side of the first reagent table 21. The first reagent table 21 and the second reagent table 22 are configured such that the first reagent container rack 310 and the second reagent container rack 320 each holding the reagent container 300 can be removably arranged. The first reagent table 21 and the second reagent table 22 are rotatably supported at a position on the upper side with respect to the bottom surface of the reagent storage 40 with a spacing by a roller or a supporting plate (not shown).

The first reagent table 21 and the second reagent table 22 are each configured so as to be rotatable both in the clockwise direction and in the counterclockwise direction, and so that each table is rotatable independent from each other. The first reagent container rack 310 and the second reagent container rack 320 for holding the reagent container 300 containing the reagent are transported in the rotating direction by the first reagent table 21 and the second reagent table 22, respectively. The reagent to be dispensed can be arranged close to the reagent dispensing units 27 to 29 when the first to third reagent dispensing units 27 to 29 dispense the reagent by transporting the reagent container 300 in the rotating direction. The reagent container 300 is formed to a cylindrical shape, and is formed with an opening for aspirating the reagent at the upper part.

Figure 9:
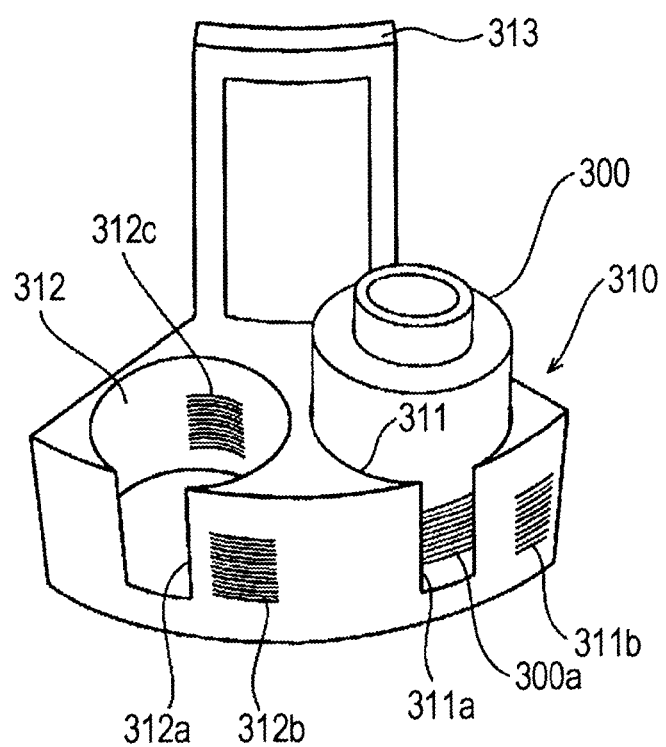
FIG. 9 is a perspective view showing one example of a first reagent container rack.

As shown in FIG. 2, five first reagent container racks 310 can be arranged in the first reagent table 21. The reagent containers 300 are arranged in a circular ring shape in the five first reagent container racks 310. As shown in FIG. 9, the first reagent container rack 310 includes two holding parts 310 and 312 for holding the reagent container 300, cut-out parts 311a and 312a arranged on the front face side of the holding parts 311 and 312, respectively, and one gripping part 313 arranged so as to project upward. Moreover, the holding parts 311 and 312 are formed into a circular shape in plan view, and are able to hold the reagent container 300 when the regent container 300 of cylindrical shape is inserted thereto. The reagent container 300 having an outer diameter smaller than the inner diameter of the holding part 311 or 312 can be held by the holding part 311 or 312 by attaching an adapter (not shown) to the holding part 311 or 312. The first reagent container rack 310 includes two types of racks formed so that the combination of the inner diameters of the holding parts 311, 312 differs. The user can respond to the reagent container 300 of various sizes by appropriately changing the type of rack. Barcodes 311b and 312b are arranged on the front face side of the outer side surface of the holding parts 311 and 312, respectively, and a barcode 312c (barcode of holding part 311 is not shown) is arranged on the inner side surface of the holding parts 311 and 312.

The two holding parts 311 and 312 can hold a plurality of reagent containers 300 containing various reagents to be added when preparing the measurement specimen from a sample one by one. That is, a maximum of ten (2×5=10) of reagent containers 300 can be arranged on the first reagent table 21. Each cut-out part 311a and 312a is arranged to read the barcode 312c on the inner side surfaces of the holding parts 311, 312 with the reagent barcode reader 33. The gripping part 313 is gripped when taking out the first reagent container rack 310 from the reagent storage 40.

Each barcode 311b and 312b includes positional information (holder number) for identifying the position of the holding parts 311 and 312. The barcodes 312c on the inner side surface include information (no reagent container information) indicating that the reagent container 300 held by the holding parts 311 and 312 does not exist. Furthermore, the barcode 300a of the reagent container 300 includes information for specifying the detailed information (information of reagent name, type of reagent container, lot number, expiration date of reagent etc.) of the reagent contained in the reagent container 300.

Figure 10:
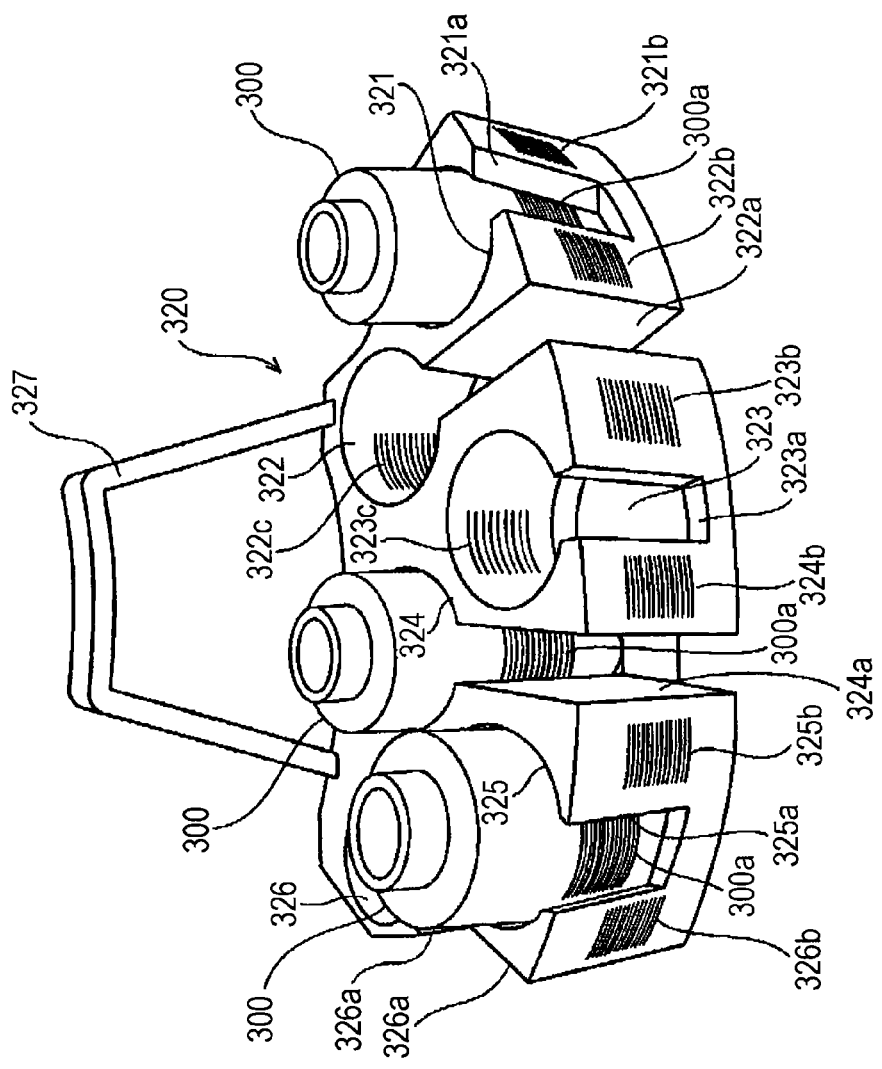
FIG. 10 is a perspective view showing one example of a second reagent container rack.

As shown in FIG. 2, five second reagent container racks 320 can be arranged in the second reagent table 22. The reagent containers 300 are arranged in a circular ring shape in the five reagent container racks 320. One of the five gaps of the second reagent container racks 320 adjacent to each other has a spacing t larger than the spacing between the other four gaps. The barcodes 311b and 312b of the first reagent container rack 310 arranged in the first reagent table 21 positioned on the inner side of the second reagent table 22 and the barcode 300a of the reagent container 300 held by the first reagent container rack 310 are read by the reagent barcode reader 330 positioned exterior to the reagent storage 40 by way of a gap having the large spacing t. As shown in FIG. 10, the second reagent container rack 320 includes six holding parts 321 to 326 for holding the reagent container 300, cut-out parts 321a to 326a arranged on the front surface side of the holding parts 321 to 326, respectively, and one gripping part 327 arranged so as to project upward. Moreover, the holding parts 321 to 326 of the second reagent container rack 320 are formed into a circular shape in plan view, similar to the first reagent container rack 310, and can hold the reagent container 300 when the regent container 300 of cylindrical shape is inserted thereto. The second reagent container rack 320 includes three types of racks formed so that the combination of the inner diameters of the holding parts 311, 312 differs. The reagent same as the reagent arranged in the first reagent container rack 310 can be arranged in the second reagent container rack 320.

Barcodes 321b and 322b are each arranged on both sides of the cut-out part 321a on the front column side. Similarly, barcodes 323b and 324b as well as barcodes 325b and 326b are arranged on both sides of the cut-put part 323a and on both sides of the cut-out part 325a, respectively. Barcodes 322c, 323c (barcodes on the inner side surfaces of the holding parts 321, 324, 325, 326 are not shown) are container on the inner side surfaces of the holding parts 321 to 326.

Each barcode 321b to 326b includes positional information (holder number) for identifying the position of the holding parts 321 to 326. The barcodes 322c, 323c on the inner side surfaces of the holding parts 321 to 326 include information (no reagent container information) indicating that the reagent container 300 held by the holding parts 321 to 326 does not exist.

The control unit 4a of the control device 4 is configured to reference the table of the reagent master, the reagent lot master, the container master, and the like stored in the hard disc 401d based on the barcode information read by the reagent barcode read 33, and acquire the reagent identification information such as the holder number, the reagent name, the lot number, the type of reagent container, the expiration date of the reagent, and the like. The acquired reagent identification information is stored in the reagent information database (not shown) stored in the hard disc 401d. The information stored in the reagent information database is reflected on the display unit 4b by the control unit 4a of the control device 4.

Figure 7:
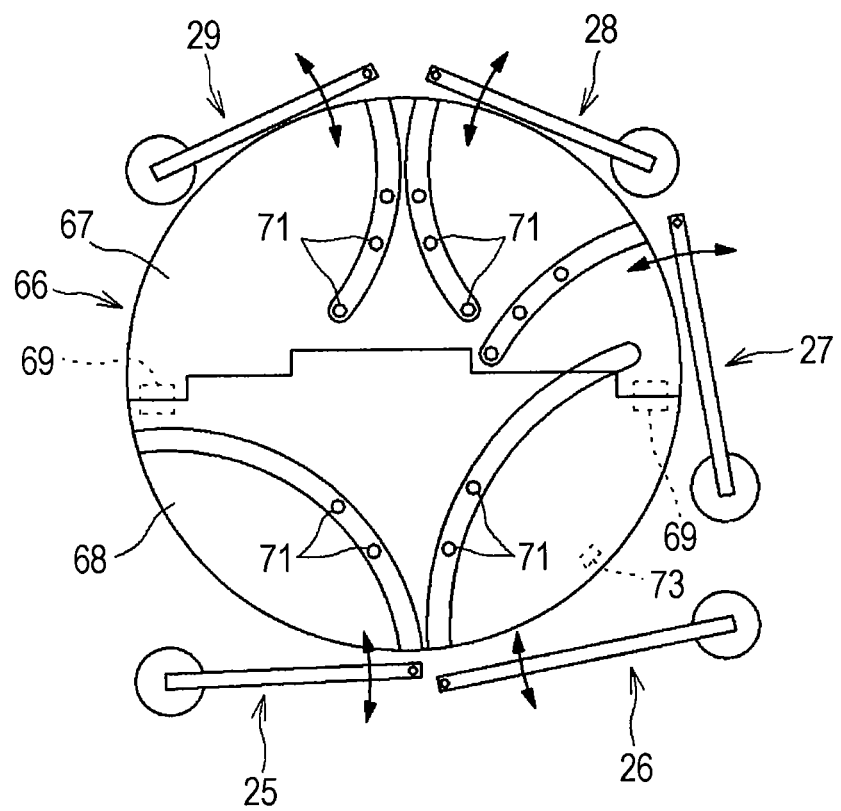
FIG. 7 is a plan view showing a lid of a reagent storage.

As shown in FIG. 6, the reagent storage 40 includes a main body 65 of a bottomed cylindrical shape including a bottom wall 63 and a peripheral wall 64 rising from the outer periphery of the bottom wall 63, and a lid 66 for blocking an upper opening of the main body 65 and functioning as an upper wall of the reagent storage 40, where a sealed space surrounded by the main body 65 and the lid 66 becomes a cooling chamber, and the reagent container 300 is arranged in the cooling chamber. As shown in FIG. 7, the lid 66 is configured by a fixed lid 67 for blocking substantially the last half of the main body 65, and a movable lid 68 that can be opened and closed for blocking substantially the first half of the main body 65. The movable lid 68 is coupled to a front edge of the fixed lid 67 in an oscillating manner through a hinge member 69.

The lid 66 of the reagent storage 40 is formed with a plurality of reagent aspirating holes 71, and is configured such that the pipettes of the first and second sample dispensing units 25, 26 and the first to third reagent dispensing units 27 to 29 (reagent aspirating units) are inserted to the reagent aspirating hole 71, and the reagent in the reagent container 300 accommodated in the reagent storage 40 is aspirated from the upper opening of the reagent container 300.

The changing of the reagent with respect to the reagent storage 40 can be carried out with respect to the entire rack by opening the movable lid 68 and opening the front half of the reagent storage 40. The reagent storage 40 includes a lid open/close detection sensor 73 for detecting the open/close of the movable lid 68. When detected by the lid open/close detection sensor 73 that the movable lid 68 is closed, the sample analyzer 1 automatically performs the reading of the barcode of the reagent container 300 held in the first reagent container rack 310 or the second reagent container rack 320, and acquires the identification information of the reagent after the change.

Figure 8:
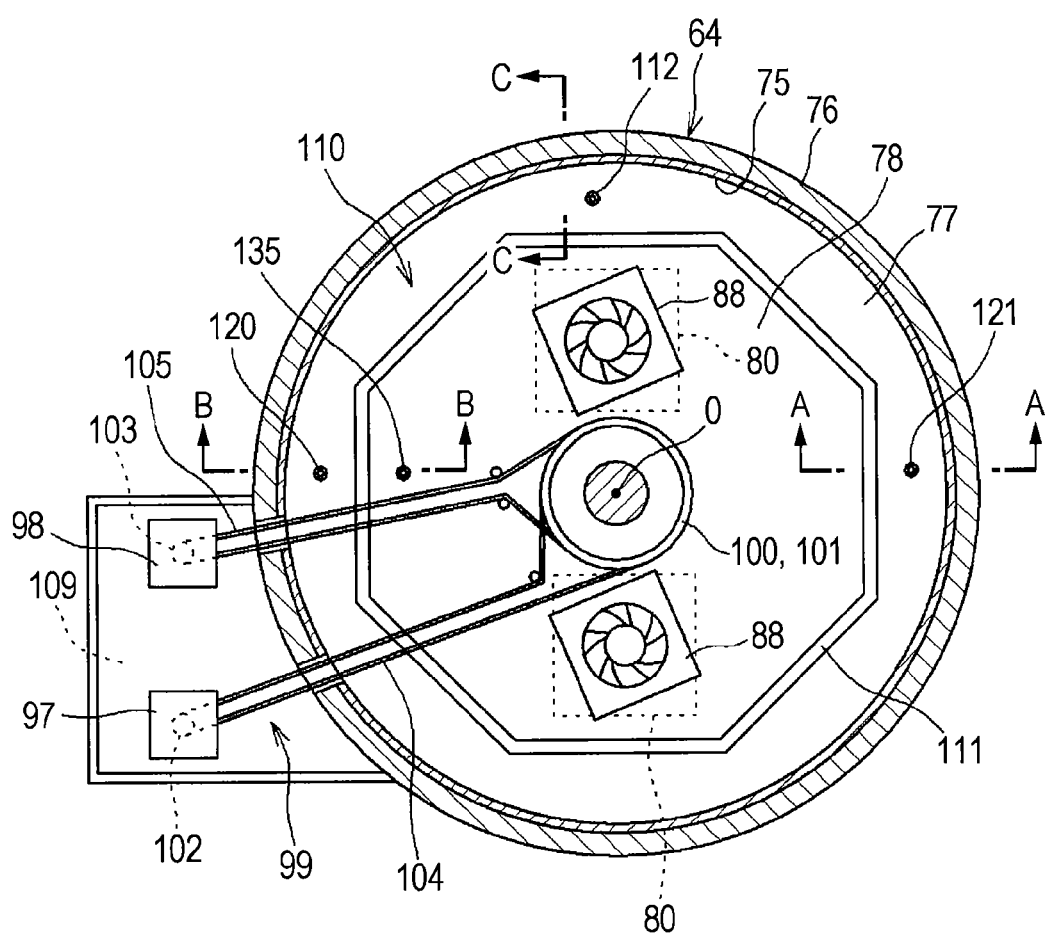
FIG. 8 is a plan cross-sectional view of the inner bottom surface of the reagent storage seen from the upper side.

As shown in FIG. 6, the peripheral wall 64 of the main body 65 of the reagent storage 40 is formed to the inner and outer two-layer structure, where the inner layer 75 is formed from a material having low heat conductivity such as synthetic resin. The outer layer 76 is a heat insulating layer having low heat conductivity. The bottom wall 63 of the main body 65 is also formed to the inner and outer two-layer structure, where the outer peripheral part 77 of the inner layer is formed from a material such as synthetic resin so as to continue from the inner layer 75 of the peripheral wall 64, and the central part of the inner layer of the bottom wall 63 is a heat transfer layer 78 formed from a material having high heat conductivity such as aluminum and is projected to the upper side than the outer peripheral part 77. The outer layer 79 of the bottom wall 63 is the heat insulating layer. The lid 66 is made from a material such as synthetic resin having low heat conductivity. As shown in FIG. 8, the heat transfer layer 78 is formed to an octagon shape in plan view. The lid 66 is formed from a material having lower heat conductivity than the inner layer 75 of the peripheral wall 64, and the inner layer 75 of the peripheral wall 64 is formed from a material having lower heat conductivity than the heat transfer layer 78 of the bottom wall 63.

As shown in FIG. 6, the heat transfer layer 78 arranged at the bottom wall 63 of the main part 65 has one part of the lower surface exposed to the lower side, where the cooler 80 is arranged on the exposed surface. In the present embodiment, two coolers 80 are arranged at symmetric positions with the center axis line O (center of rotation of first and second reagent tables 21, 22) of the reagent storage 40 as the center. The cooler 80 of the present embodiment uses the peltier element 81, where a heat sink 82 is arranged on the lower surface (heat exhaust side) of the peltier element 81, and a heat dissipation fan 83 is arranged on the lower surface of the heat sink 82. The cooler 80 uses the heat transfer layer 78 itself for the cooling medium by directly cooling the heat transfer layer 78 of the main body 65 having high heat conductivity, thereby cooling the air in the reagent storage 40. The cooler 80 is not limited to that which uses the peltier element 81, and may be that which is configured to cool the heat transfer layer 78 through air cooling or water cooling.

An intake duct 85 for taking in the air outside the sample analyzer 1 is formed on the lower side of the reagent storage 40, and the heat sink 82 is arranged in the intake duct 85. An exhaust duct 86 for exhausting the air to outside the sample analyzer 1 is formed on the lower side of the intake duct 85, and the heat dissipation fan 83 is connected to the exhaust duct 86. The outside air is taken in from the intake duct 85 to the heat sink 82 by the drive of the heat dissipation fan 83, and warm wind is exhausted to the exhaust duct 86 after performing heat exchange in the heat sink 82. The intake port of the intake duct 85 and the exhaust port of the exhaust duct 86 are opened at the rear surface and the side surface of the sample analyzer 1, so that the warm wind exhausted from the exhaust duct 86, in particular, does not directly hit the user using the sample analyzer 1.

In the reagent storage 40, a flowing fan (circulating section) 88 is arranged between the first reagent table 21 and the second reagent table 22, and the bottom wall 63 (inner bottom surface) of the reagent storage 40. In the present embodiment, two flowing fans 88 are each arranged at positions corresponding to the upper side of the coolers 80. Therefore, the two flowing fans 88 are also symmetrically arranged with the center axis line O of the reagent storage 40 as the center.

Figure 11:
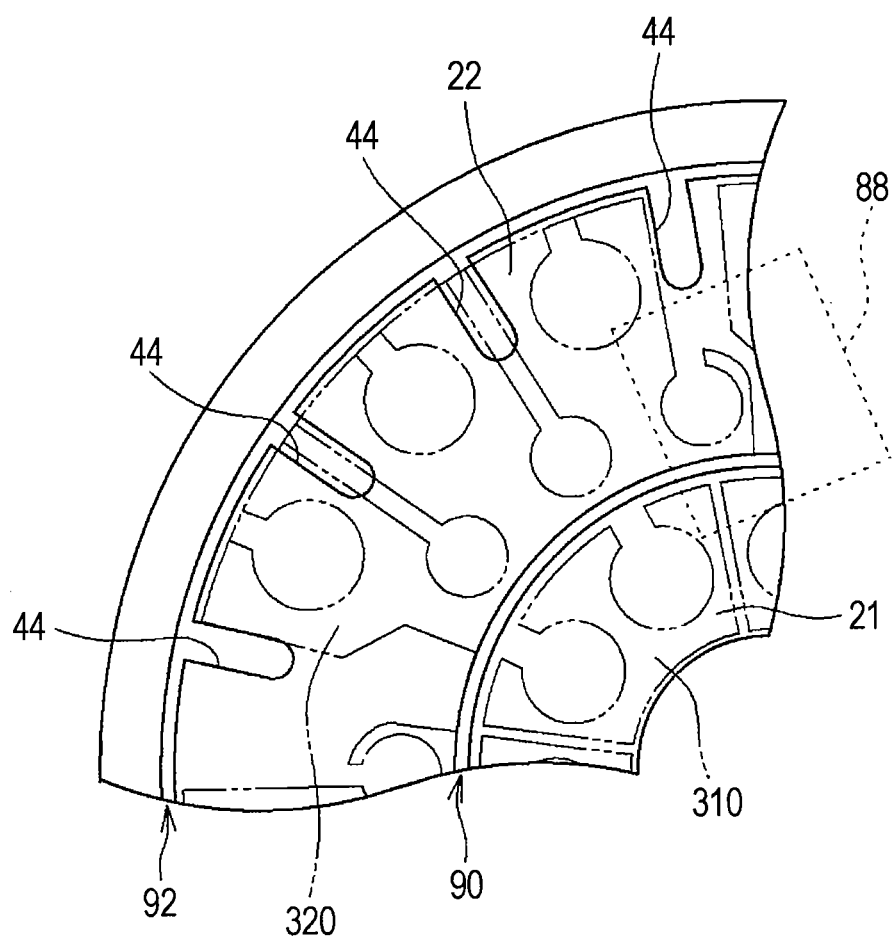
FIG. 11 is a plan view showing one part of the reagent table in an enlarged manner.

The flowing fan 88 is configured to blow out the air taken in from the upper side to the lower side. The air flow generated by the flowing fan 88 is thus directly blown against the portion directly cooled by the cooler 80 in the heat transfer layer 78. The air flow thus can be efficiently cooled. As shown in FIG. 2, FIG. 11, and the like, the flowing fan 88 is arranged at the lower position of the first gap 90 formed between the outer peripheral part of the first reagent table 21 and the inner peripheral part of the second reagent table 22. Thus, the air on the upper side than the first and second reagent tables 21, 22 is taken in by the flowing fan 88 through the first gap 90 and an opening 38a of the rotation supporting portion 38, to be described later.

The air flow generated by the flowing fan 88 is blown against the heat transfer layer 78, and then flows radially outward, passes through a second gap 92 between the peripheral wall 64 (inner side surface) of the reagent storage 40 and the second reagent table 22, and flows to the upper side of the second reagent table 22. Thereafter, the air flow passes between the reagent container 300 arranged on the first reagent table 21 and the reagent container 300 arranged on the second reagent table 22, and again flows to the lower side from the first gap 90, thus circulating inside the reagent storage 40. The reagent in the reagent container 300 arranged on the first and second reagent tables 21, 22 is cooled to the desired temperature such as about 10° C. with the air circulated by the flowing fan 88.

The flowing fan 88 is arranged between the lower surface of the first, second reagent table 21, 22 and the bottom wall 63 of the reagent storage 40, and is arranged at a position distant as much as possible from the lid 66. Thus, the outside air less likely to be taken in from the reagent aspirating hole 71 (see FIG. 7) formed in the lid 66.

The cooler 80 and the flowing fan 88 are arranged in plurals and are arranged at symmetric positions with the center axis line O as the center, and thus the air cooled in the reagent storage 40 can be uniformly circulated. The flowing fan 88 is arranged at a position corresponding to the upper side of the cooler 80, and thus a strong air can hit against one part of the heat transfer layer 78 directly cooled by the cooler 80 and colder air can be efficiently circulated. Thus, the cold air can be easily delivered to the reagent container at any position on the reagent table, and enlargement of the reagent table involved in the increase in the number of reagent containers can be responded.

The cooler 80 and the flowing fan 88 are not limited to two, and may be three or more. In this case, the air cooled in the reagent storage 40 can be uniformly circulated by arranging a plurality of coolers 80 and flowing fans 88 at equal interval around the center axis line O.

As the heat transfer layer 78 is arranged only on the bottom wall 63 of the reagent storage 40, and the peripheral wall 64 is formed from a material having low heat conductivity, the inside of the reagent storage 40 is prevented from being over-cooled, and the generation of dew condensation at the peripheral wall 64 can be prevented.

As shown in FIG. 11, a plurality of recesses 44 recessed in the radial direction is formed with an interval in the peripheral direction at the outer peripheral part of the second reagent table 22. As shown in FIG. 6, the reagent barcode reader 33 is configured to read the barcode attached to the reagent container 300 as well as the first and second reagent container racks 310, 320 from obliquely lower side, and the recess 44 is formed so that the outer peripheral part of the second reagent table 22 does not get in the way when reading the barcodes attached to the reagent container 300 as well as the first and second reagent container racks 310, 320 with the reagent barcode reader 33. The second gap 92 between the outer peripheral part of the second reagent table 22 and the inner side surface of the reagent storage 40 is partially extended by the recess 44, and hence the air flow more easily passes through the second gap 92 and more smooth air circulation can be realized.

A lid heater 95 (see FIG. 6) is arranged inside the lid 66, and the lid 66 is warmed by the lid heater 95. Thus, even if outside air enters from the reagent aspirating hole 71, for example, the moisture contained in the outside air can be prevented from dew condensing at the lid 66.

As shown in FIG. 6 and FIG. 8, the first and second reagent tables 21, 22 are rotatably driven by a first drive unit 97 and a second drive unit 98 including a stepping motor, and the like. The first and second drive units 97, 98 are arranged at the side of the reagent storage 40, and are connected to the first and second reagent tables 21, 22, respectively, through a power transmission mechanism 99. The power transmission mechanism 99 is configured by a first driven pulley 100, a second driven pulley 101, a first drive pulley 102, a second drive pulley 103, a first transmission belt 104, and a second transmission belt 105. The first driven pulley 100 and the second driven pulley 101 are arranged on the center axis line O of the reagent storage 40, and are coupled in an integrally rotatable manner to a rotation shaft 200 of the first reagent table 21 and a rotation shaft 201 of the second reagent table 22, respectively.

As shown in FIG. 6, the rotation supporting portion 38 for supporting the second reagent table 22 from the lower side is arranged on the lower side of the second reagent table 22. The rotation supporting portion 38 is fixed to the second reagent table 22 and the rotation shaft 201 of the second reagent table 22, and is configured to integrally rotate the second reagent table 22 with the rotation of the rotation shaft 201. The rotation supporting portion 38 includes a plurality of openings 38a with a spacing in the peripheral direction. Such openings 38a are arranged at the positions on the lower side of the first gap 90 formed between the outer peripheral part of the first reagent table 21 and the inner peripheral part of the second reagent table 22.

The rotation shaft 201 of the second reagent table 22 is formed to a tubular shape, and the rotation shaft 200 of the first reagent table 21 is passed through the inside of the rotation shaft 201 of the second reagent table 22 and fixed to the first reagent table 21. The first reagent table 21 thus rotates with the rotation of the rotation shaft 201.

The first drive pulley 102 is attached to an output shaft of the first drive unit 97, and the second drive pulley 103 is attached to an output shaft of the second drive unit 98. The first transmission belt 104 is wounded to the first driven pulley 100 and the first drive pulley 102, and the second transmission belt 105 is wounded to the second driven pulley 101 and the second drive pulley 103.

The peripheral wall 64 of the reagent storage 40 is formed with a first insertion port 107 and a second insertion port 108 for receiving the first transmission belt 104 and the second transmission belt 105. A heat insulating chamber 109 surrounded with heat insulating material is formed at the side of the reagent storage 40, which heat insulating chamber 109 is communicated to the reagent storage 40 through the first insertion port 107 and the second insertion port 108. The first drive pulley 102 and the second drive pulley 103 are arranged in the heat insulating chamber 109. Thus, the cooled air in the reagent storage 40 retains inside the heat insulating chamber even if leaked from the first and second insertion ports 107, 108, and hence the degradation of the cooling efficiency of the reagent storage 40 can be prevented.

The first drive unit 97 and the second drive unit 98 are arranged at the side of the reagent storage 40, and hence the dew condensation water generated in the reagent storage 40 and the liquid in the liquid storing section 110 do not spill on the first drive unit 97 and the second drive unit 98 even if leaked out to the lower side of the reagent storage 40, thereby preventing the first drive unit 97 and the second drive unit 98 from breaking down.

The diameter of the rotation shafts of the first and second reagent tables 21, 22 can be made large since the flowing fan 88 is arranged at the central portion of the reagent arrangement section 59. Thus, the first and second reagent tables 21, 22 can be rotated at a small driving force, and the first and second reagent tables 21, 22 can be positioned at high accuracy.

The first drive unit 97 and the second drive unit 98 are not limited to being arranged at the side of the reagent storage 40, and may be arranged anywhere as long as it is a region on the outer side of the reagent storage 40 other than the lower side. The power transmission mechanism 99 is a winding transmission mechanism including the pulleys and the transmission belt, but is not limited thereto, and may use other power transmission mechanism such as a gear transmission mechanism.

The task of changing and adding the reagent container 300 to the reagent storage 40 can be carried out by opening the movable lid 68 (see FIG. 7). In this case, the operation of the flowing fan 88 arranged in the reagent storage 40 is stopped. Specifically, when the lid open/close detection sensor 73 (see FIG. 3 and FIG. 7) detects that the movable lid 68 is opened, such detection information is input to the control unit 501, and the control unit 501 controls to stop the operation of the flowing fan 88. The outside air is thus prevented from being actively taken into the reagent storage 40, and the moisture contained in the outside air can be prevented from dew condensing and attaching to the inner surface of the reagent storage 40. The control unit 501 may perform the control to stop not only the flowing fan 88 but also the cooler 80 when the movable lid 68 is opened.

As shown in FIG. 8, the heat transfer layer 78 is arranged at the central part of the bottom wall 63 of the reagent storage 40, and the liquid storing section 110 is arranged on the outer side in the radial direction thereof to surround the outer periphery of the heat transfer layer 78. Specifically, as shown in FIG. 6, the heat transfer layer 78 is arranged at the bottom wall 63 of the reagent storage 40 so as to project out to the upper side, where an annular groove opened to the upper side is formed between the outer peripheral edge of the heat transfer layer 78 and the peripheral wall 64 of the reagent storage 40. Such a groove is the liquid storing section 110.

The liquid storing section 110 receives and stores liquid other than the reagent, or the cleaning solution (RO water) to supply to the pipette cleaners 36*a* to 36*e* in the present embodiment. The air cooled in the reagent storage 40 directly touches the surface of the stored liquid since the liquid storing section 110 is opened to the upper side. The cleaning solution of the pipette is stored in the cleaning solution tank 113 (see FIG. 14) arranged in the measurement device 2 at the exterior of the reagent storage 40, and hence the liquid (cleaning solution) stored in the liquid storing section 110 has a temperature higher than the temperature in the reagent storage 40, that is, the temperature of the reagent.

The air cooled by the cooler 80 is circulated in the reagent storage 40 by the flowing fan 88, and hence the reagent may possibly evaporate when the cooled air touches the reagent in the reagent container 300. When the reagent evaporates, the component concentration changes, which may adversely affect the analysis result of the sample.

In the present embodiment, liquid other than the reagent is stored in the liquid storing section 110 formed in a relatively wide range of the reagent storage 40, and such liquid has a higher temperature than the reagent, whereby the evaporation of the liquid in the liquid storing section 110 is mainly promoted and the temperature in the reagent storage 40 rises. The evaporation of the reagent in the reagent container 300 thus can be suppressed.

As shown in FIG. 6 and FIG. 8, a heat insulating member 111 is attached to the outer peripheral edge of the heat transfer layer 78, so that the liquid in the liquid storing section 110 does not directly contact the heat transfer layer 78 and cooled by the heat transfer layer 78. The liquid in the liquid storing section 110 is thus prevented from becoming difficult to evaporate.

Furthermore, the air flow easily contacts the liquid stored in the liquid storing section 110 and the evaporation of the liquid can be promoted since the liquid storing section 110 is arranged immediately on the outer side of the heat transfer layer 78 to which the air flow generated by the flowing fan 88 is blown against.

Figure 14:
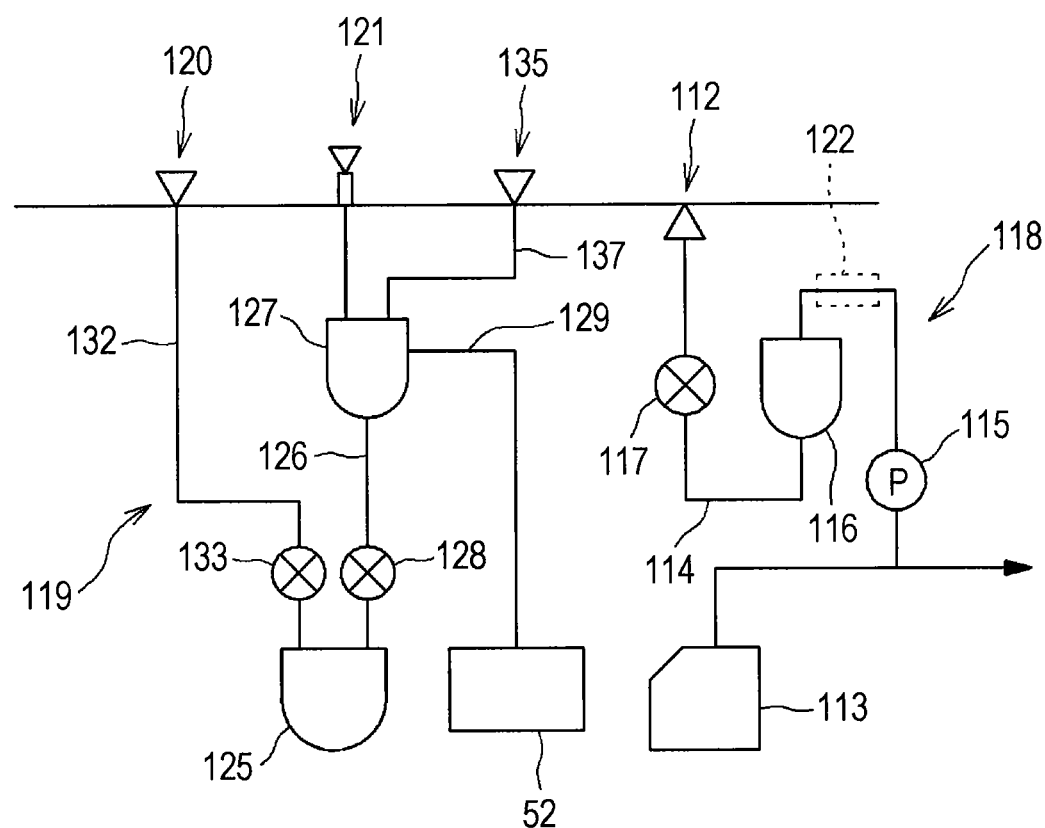
FIG. 14 is a schematic view showing a configuration of a liquid supply unit and a liquid discharge unit.

As shown in FIG. 8, the liquid is supplied to the liquid storing section 110 from the supply port 112 formed at the bottom surface. As shown in FIG. 14, the supply port 112 is connected to the cleaning solution tank 113 accommodating the pipette cleaning solution through the supply piping 114 in the present embodiment. The supply piping 114 that connects the cleaning solution tank 113 and the supply port 112 includes a pump 115, a relay chamber 116, and an open/close valve 117. The cleaning solution pumped up from the cleaning solution tank 113 by the operation of the pump 115 is once stored in the relay chamber 116, and supplied to the supply port 112 when the open/close valve 117 is opened.

Figure 17:
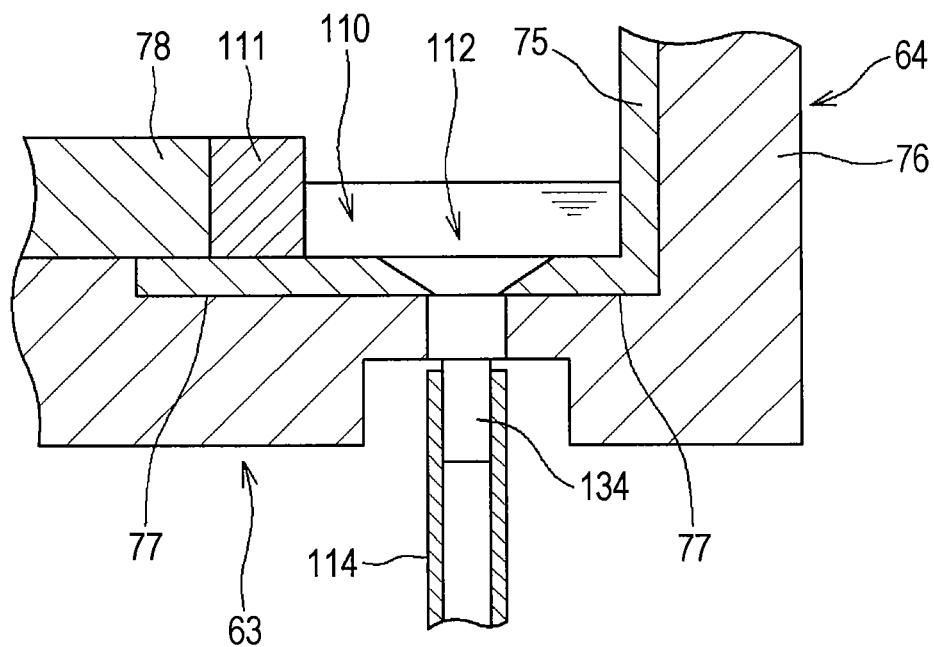
FIG. 17 is a cross-sectional view taken along line C-C of FIG. 8.

FIG. 17 is a cross-sectional view taken along line C-C of FIG. 8. The supply port 112 is a hole formed at the bottom surface of the liquid storing section 110, where such a hole communicates to a connection tube 134 attached to the bottom wall 63 of the reagent storage 40, and the supply piping 114 is connected to the connection tube 134.

Therefore, the pump 115, the relay chamber 116, the open/close valve 117, the supply port 112, and the like configure a liquid supply unit 118 for supplying the liquid to the liquid storing section 110. The pump 115 may be a diaphragm type pump 115 that operates by pneumatic source. The liquid supply unit 118 (pump 115, open/close valve 117, etc.) is operation controlled by the control unit 501 (see FIG. 3).

As shown in FIG. 8, the liquid stored in the liquid storing section 110 is discharged from the liquid discharge port formed at the bottom surface. In the present embodiment, two liquid discharge ports are provided, where one is an all liquid discharge port 120 capable of discharging all the liquid in the liquid storing section 110, and the other is a constant-amount liquid discharge port 121 for discharging the redundant liquid exceeding a predetermined amount in the liquid storing section 110.

Figure 12:
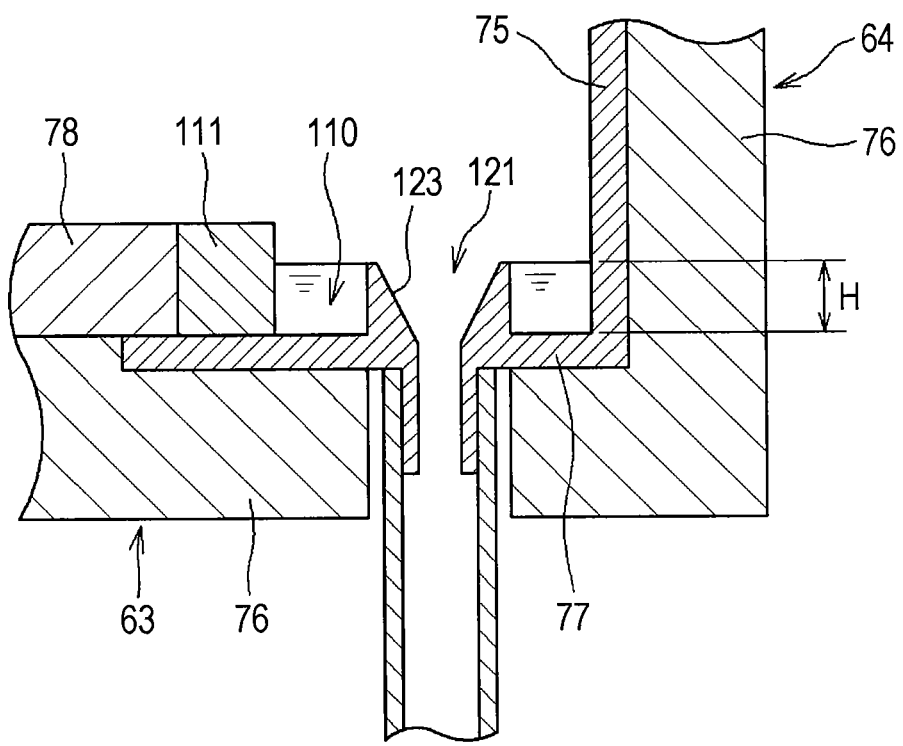
FIG. 12 is a cross sectional view taken along line A-A of FIG. 8.

FIG. 12 is a cross sectional view taken along line A-A of FIG. 8. A cylindrical dam member 123 projecting out from the bottom surface of the liquid storing section 110 is arranged at the peripheral edge of the constant-amount liquid discharge port 121. The dam member 123 is formed lower than the depth of the liquid storing section 110 (thickness of heat transfer layer 78), where the liquid can be stored in the liquid storing section 110 up to the height H of the dam member 123, but the liquid exceeding the dam member 123 is discharged from the constant-amount discharge port 121.

As shown in FIG. 14, the constant-amount liquid discharge port 121 is connected to the liquid discharge chamber 125 through a liquid discharge piping 126, and the relay chamber 127 and the open/close valve 128 are arranged on the liquid discharge piping 126. The liquid discharged from the constant-amount liquid discharge port 121 is once stored in the relay chamber 127 and then discharged to the liquid discharge chamber 125 by opening the open/close valve 128. An overflow tube 129 is connected to the relay chamber 127, which overflow tube 129 is connected to the cuvette discarding unit 52 for discarding used cuvettes. Therefore, the liquid stored in the relay chamber 127 by greater than or equal to a predetermined amount is discarded to the cuvette discarding unit 52.

Figure 13:
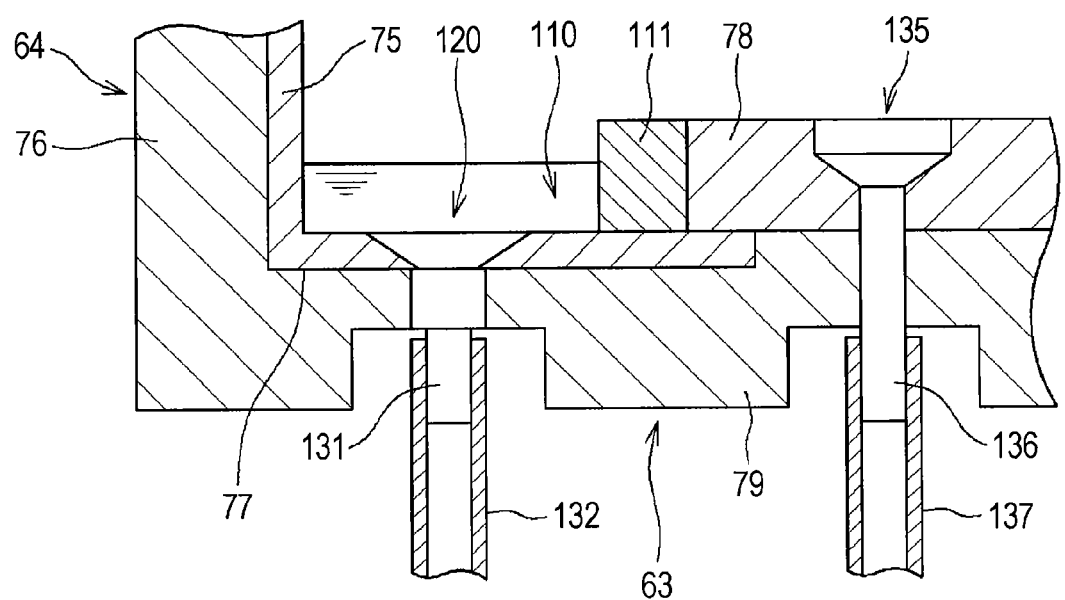
FIG. 13 is a cross-sectional view taken along line B-B of FIG. 8.

FIG. 13 is a cross-sectional view taken along line B-B of FIG. 8. The all liquid discharge port 120 is a hole formed at the bottom surface of the liquid storing section 110, where such a hole communicates to a connection tube 131 attached to the bottom wall 63 of the reagent storage 40, and the liquid discharge piping 132 is connected to the connection tube 131. As shown in FIG. 14, the liquid discharge piping 132 is connected to the liquid discharge chamber 125. The open/close valve 133 is arranged on the liquid discharge tube 132, where the liquid in the liquid storing section 110 can be discharged from the all liquid discharge port 120 by opening the open/close valve 133.

Therefore, in the present embodiment, the liquid discharge unit 119 for discharging the liquid in the liquid storing section 110 is configured by the constant amount liquid discharge port 121, the all liquid discharge port 120, the liquid discharge piping 126, 132, the relay chamber 127, the liquid discharge chamber 125, and the open/close valve 128, 133, and the like. The liquid discharge section 119 (open/close valve 128, 133, etc.) is operation controlled by the control unit 501 (see FIG. 3).

The control device 4 has a function of accepting a supply instruction of liquid by the liquid supply unit 118 and a discharge instruction of liquid by the liquid discharge unit 119, and the control unit 501 of the measurement device 2 operation controls the liquid supply unit 118 and the liquid discharge unit 119 based on each instruction accepted by the control device 4.

As shown in FIG. 13, an inner liquid discharge port 135 is formed at the upper surface of the heat transfer layer 78. The inner liquid discharge port 135 is arranged to discharge the dew condensation water attached to the heat transfer layer 78. The inner liquid discharge port 135 communicates to the connection tube 136 attached to the bottom wall 63 of the reagent storage 40, and the liquid discharge piping 137 is connected to the connection tube 136.

As shown in FIG. 14, the liquid discharge piping 137 is connected to the relay chamber 127, and the liquid in the heat transfer layer 78 is discharged to the relay chamber 127 through the liquid discharge piping 137 from the inner liquid discharge port 135, and discharged to the liquid discharge chamber 125 by opening the open/close valve 128.

The sample analyzer 1 according to the present embodiment has two operation modes regarding the cooling of the reagent in the reagent storage 40. The two operation modes are a cold storage mode of continuously cooling the reagent storage (cooling reagent) even while the sample analyzer 1 is shut down, and a normal mode of stopping the cooling of the reagent storage 40 with the shutdown of the sample analyzer 1.

Figure 15:
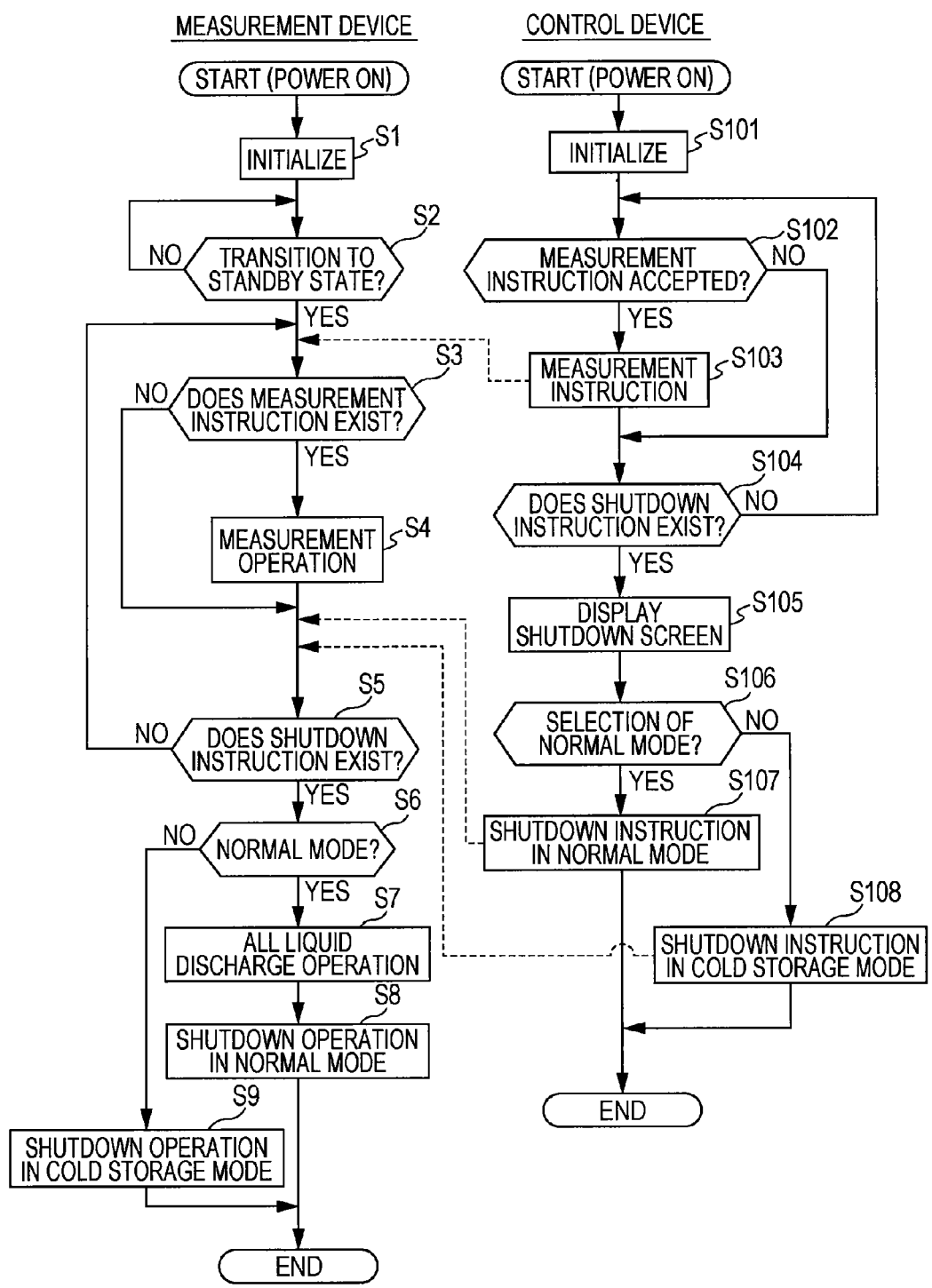
FIG. 15 is a flowchart showing the operation of the sample analyzer.

FIG. 15 is a flowchart showing the operation of the sample analyzer 1 including the selection of two operation modes. First, when the power of the measurement device 2 is turned ON, initialization of the program stored in the control unit 501, the origin recovery operation of each dispensing unit drive unit 141 and each table drive unit 142 to 144, and the like are performed in step S1. When the power of the control device 4 is turned ON, the initialization of the program stored in the control unit 4a is also performed in step S101.

In step S2, the control unit 501 of the measurement device 2 determines whether or not the measurement device 2 is in the standby state, that is, in a state capable of starting the measurement. On the other hand, the control device 4 determines whether the measurement instruction from the user is accepted. When determining that the measurement instruction is accepted, the measurement device 4 transmits a measurement instruction to the measurement device 2 in step S103. When determining that the measurement instruction is not accepted, the control device 4 proceeds the process to step S104.

In step S3, the control unit 501 of the measurement device 2 determines whether or not the measurement instruction from the control device 4 is received. The control unit 501 proceeds the process to step S4 when determining that the measurement instruction is received, and proceeds the process to step S5 when determining that the measurement instruction is not received. In step S4, the measurement device 2 performs a predetermined measurement operation (analyzing operation) based on the measurement instruction.

In step S104, the control device 4 determines whether or not the shutdown instruction (operation stop instruction) is accepted from the user. The control device 4 returns the process to step S102 when determining that the shutdown instruction is not accepted. The control device 4 proceeds the process to step S105 and displays a shutdown screen on the display unit 4b when determining that the shutdown instruction is accepted. The shutdown screen includes a selection screen for the normal mode and the cold storage mode.

In step S106, the control device 4 determines whether or not the normal mode is selected. The control device 4 proceeds the process to step S107 when determining that the normal mode is selected, and transmits the shutdown instruction in the normal mode to the measurement device 2. The control device 4 proceeds the process to step S108 when determining that the normal mode is not selected, that is, when determining that the cold storage mode is selected, and transmits the shutdown instruction in the cold storage mode to the measurement device 2.

In step S5, the control unit 501 of the measurement device 2 determines whether or not the shutdown instruction is received from the control device 4. The control unit 501 of the measurement device 2 returns the process to step S3 when determining that the shutdown instruction is not received. The control unit 501 proceeds the process to step S6 when determining that the shutdown instruction is received.

In step S6, the control unit 501 of the measurement device 2 determines whether or not the shutdown instruction is the normal mode. The control unit 501 proceeds the process to step S7 when determining as the normal mode, and proceeds the process to step S9 when determining as not the normal mode (as the cold storage mode).

In step S7, the control unit 501 of the measurement device 2 operation controls the liquid discharge unit 119 so that all the liquid in the liquid storing section 110 in the reagent storage 40 are discharged. In other words, all the liquid in the liquid storing section 110 is discharged from the all liquid discharge port 120 to the liquid discharge chamber 125 by opening the open/close valve 133, as shown in FIG. 14. The operation of the cooler 80 and the flowing fan 88 is also stopped. In step S8, the shutdown of the measurement device 2 is executed, and the process is terminated.

In step S9, the shutdown operation in the cold storage mode is carried out. In other words, the measurement device 2 is shut down and the process is terminated without discharging the liquid in the liquid storing section 110 or stopping the operation of the cooler 80 and the flowing fan 88. In the cold storage mode, the reagent storage 40 operates and stores the reagent cold even if the power of the measurement device 2 is turned OFF.

At the time of the operation of the sample analyzer 1 or when stopped by the cold storage mode. The reagent in the reagent storage 40 is stored cold, but if the liquid stored in the liquid storing section 110 is retained for a long time, such liquid is cooled by the cold air in the reagent storage 40, and gradually becomes difficult to evaporate, thereby lowering the function of raising the humidity in the reagent storage 40. Furthermore, if the liquid is remained stored in the liquid storing section 110, moss, bacteria, and the like may produce in the stored liquid. Thus, the control unit 501 of the measurement device 2 is configured to change the liquid in the liquid storing section 110 by controlling the liquid supply unit 118.

Figure 16:
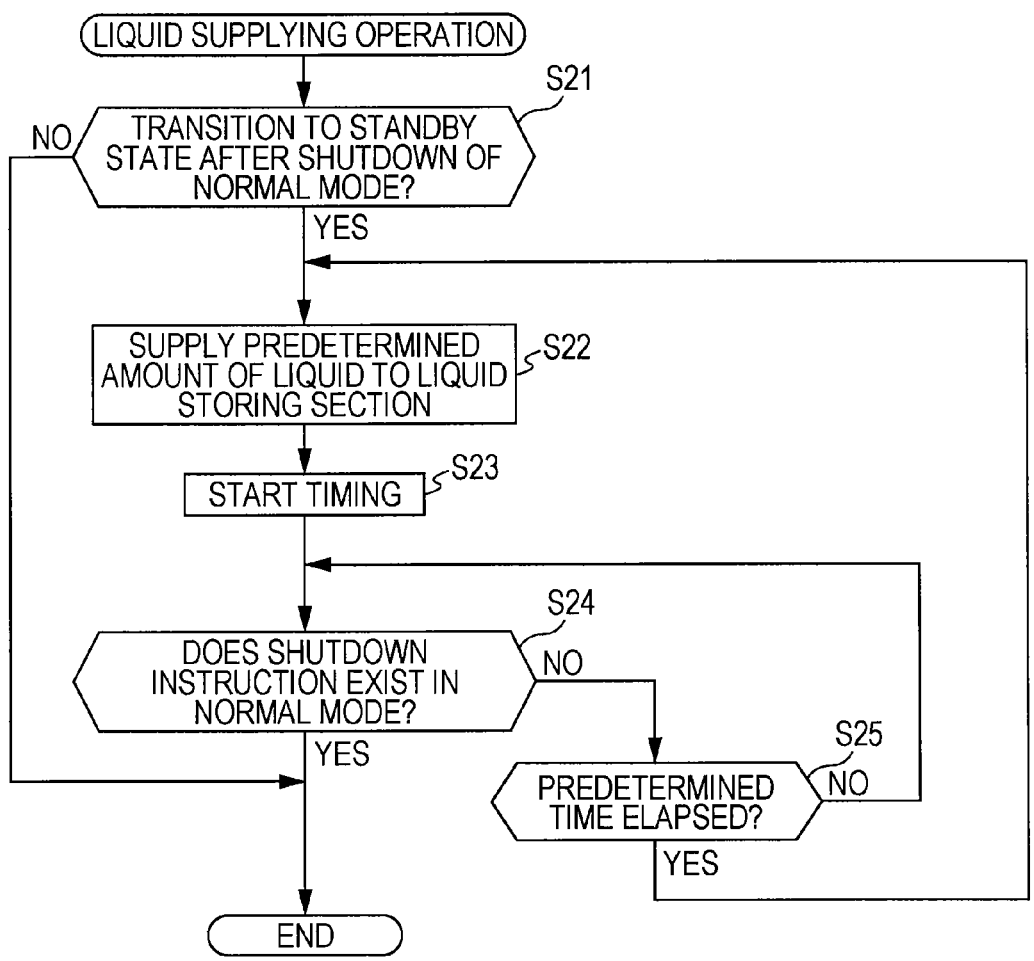
FIG. 16 is a flowchart showing the operation of the measurement device on the supply of liquid to the liquid storing section at the time of the operation of the sample analyzer.

FIG. 16 is a flowchart showing the operation of the measurement device 2 on the supply of liquid (include changing of liquid) to the liquid storing section 110 at the time of the operation of the sample analyzer 1. First, in step S21, the control unit 501 determines whether or not the measurement device 2 transitioned to the standby state after the shutdown of the normal mode.

The liquid storing section 110 is empty when transitioned to the standby state after the shutdown of the normal mode, and thus the control unit 501 operation controls the liquid supply unit 118 to supply a predetermined amount of liquid to the liquid storing section 110 in step S22.

In step S23, the control unit 501 starts the measurement of the elapsed time after the liquid supply. In step S24, the control unit 501 determines whether or not the shutdown instruction in the normal mode is received, and terminates the process on the liquid supply with respect to the liquid storing section 110 when determining that the shutdown instruction is received. When determining that the shutdown instruction in the normal mode is not received in step S24, the control unit 501 further determines whether or not a predetermined time has elapsed in step S25. The process returns to step S24 when determined that the predetermined time has not elapsed, and the process returns to step S22 when determined that the predetermined time has elapsed. A predetermined amount of liquid is again supplied to the liquid storing section 110 in step S22.

Therefore, new liquid is supplied every predetermined time to the liquid storing section 110, and the redundant old liquid is discharged from the constant amount liquid discharge port 121. The liquid in the liquid storing section 110 can be suitably changed before the liquid in the liquid storing section 110 reaches the same temperature as the reagent by the cold air in the reagent storage 40 or without the low temperature state lasting for a long time, and the evaporation of the liquid is promoted. The moss and the bacteria are also suppressed from producing at the liquid. The supply of liquid every predetermined time is also carried out after the shutdown in the cold storage mode.

The supply of liquid to the liquid storing section 110 may not be every predetermined time, and may be continuously carried out during the operation of the sample analyzer 1 or after the shutdown by the cold storage mode. The temperature of the liquid in the liquid storing section 110 thus can be constantly maintained at a temperature higher than the reagent.

Since the changing of the liquid with respect to the liquid storing section 110 described above is carried out with the newly supplied liquid and the originally remaining liquid mixing with each other, it is difficult to completely change the liquid in the liquid storing section 110. Thus, the all liquid discharge port 120 may be used to change the liquid with respect to the liquid storing section 110 in the liquid supplying operation described in FIG. 16. In this case, all the liquid stored in the liquid storing section 110 are discharged from the all liquid discharge port 120, and thereafter, a predetermined amount of liquid may be supplied by the liquid supply unit 118 in step S22 after step S25. In this way, the liquid in the liquid storing section 110 can be completely changed. In this case, however, the operation control of not only the liquid supply unit 118 but also the liquid discharge unit 119 (open/close valve 133) is also necessary, and thus the liquid is preferably changed using the constant amount liquid discharge port 121 in terms of simplifying the control.

The supply piping 114 for flowing the cleaning solution from the cleaning solution tank 113 to the liquid storing section 110 may be warmed with a heater to supply liquid of higher temperature to the liquid storing section 110. For instance, as shown in FIG. 14, the heater 122 may be arranged along one part of the supply piping 114. The supply piping 114 may be warmed by exhaust heat from the cooler 80 by passing the supply piping 114 through the air exhaust duct 86. In the latter case, the energy consumption barely increases and thus is economical since a new heat source is not necessary.

[Verification of Effect by Liquid Storing Section]

The inventors of the present invention conducted an experiment to verify the effect of arranging the liquid storing section 110, that is, the effect of suppressing evaporation of the reagent. The following table 1 shows the experiment result.

TABLE 1

| | RACK | CONTAINER NO. | CONTAINER TYPE | LIQUID AMOUNT | $0^{TH}$ HOUR (g) | $24^{TH}$ HOUR (g) | WITH WATER SUPPLY/ AMOUNT OF EVAPORATION (g) | WITH WATER SUPPLY/ AMOUNT OF EVAPORATION (μL) | NO WATER SUPPLY/ AMOUNT OF EVAPORATION (μL) | COMPARISON WITH NO WATER SUPPLY (%) |
|---|---|---|---|---|---|---|---|---|---|---|
| SECOND REAGENT CONTAINER RACK | A | 1 | GW15 | 15 mL | 30.49637 | 30.39634 | 0.10003 | 100.03 | 266.06 | 37.6 |
| | | 2 | Cup | 4 mL | 5.72329 | 5.37713 | 0.34616 | 346.16 | 700.07 | 49.4 |
| | | 3 | I RC5 | 5 mL | 15.97910 | 15.95273 | 0.02637 | 26.37 | 125.48 | 21.0 |
| | | 4 | SLD | 4 mL | 7.33048 | 7.23353 | 0.09695 | 96.95 | 214.04 | 45.3 |
| | | 5 | S I RC17 | 10 mL | 25.34675 | 25.31357 | 0.03318 | 33.18 | 69.55 | 47.7 |
| | | 6 | GW5 | 5 mL | 14.04920 | 13.97037 | 0.07883 | 78.83 | 120.49 | 65.4 |
| | B | 1 | GW15 | 15 mL | 30.43633 | 30.33197 | 0.10436 | 104.36 | 281.73 | 37.0 |
| | | 2 | Cup | 4 mL | 5.71337 | 5.32475 | 0.38862 | 388.62 | 706.93 | 55.0 |
| | | 3 | I RC5 | 5 mL | 16.09192 | 16.05314 | 0.03878 | 38.78 | 103.7 | 37.4 |
| | | 4 | P-FDP | 5 mL | 9.90475 | 9.83191 | 0.07284 | 72.84 | 220.00 | 33.1 |
| | | 5 | S I RC17 | 10 mL | 25.22902 | 25.20473 | 0.02429 | 24.29 | 99.55 | 24.4 |
| | | 6 | GW5 | 5 mL | 13.68963 | 13.64309 | 0.04654 | 46.54 | 83.08 | 56.0 |
| | C | 1 | GW15 | 15 mL | 30.52583 | 30.41315 | 0.11268 | 112.68 | 220.55 | 51.1 |
| | | 2 | Cup | 4 mL | 5.70282 | 5.42363 | 0.27919 | 279.19 | 415.04 | 67.3 |
| | | 3 | I RC5 | 5 mL | 15.87304 | 15.83775 | 0.03529 | 35.29 | 60.66 | 58.2 |
| | | 4 | SLD | 4 mL | 7.32451 | 7.23795 | 0.08656 | 86.56 | 180.52 | 48.0 |
| | | 5 | S I RC17 | 10 mL | 25.06921 | 25.04374 | 0.02547 | 25.47 | 74.68 | 34.1 |
| | | 6 | GW5 | 5 mL | 13.91956 | 13.8935 | 0.02606 | 26.06 | 104.13 | 25.0 |

TABLE 1-continued

|  | RACK | CONTAINER NO. | CONTAINER TYPE | LIQUID AMOUNT | $0^{TH}$ HOUR (g) | $24^{TH}$ HOUR (g) | WITH WATER SUPPLY/ AMOUNT OF EVAPO- RATION (g) | WITH WATER SUPPLY/ AMOUNT OF EVAPO- RATION (μL) | NO WATER SUPPLY/ AMOUNT OF EVAPO- RATION (μL) | COM- PARISON WITH NO WATER SUPPLY (%) |
|---|---|---|---|---|---|---|---|---|---|---|
| FIRST | a | 1 | GW15 | 15 mL | 30.43568 | 30.28283 | 0.15285 | 152.85 | 418.61 | 36.5 |
| REAGENT | b | 1 | Cup | 4 mL | 5.69269 | 5.3957 | 0.29699 | 296.99 | 587.42 | 50.6 |
| CON- | c | 1 | I RC5 | 5 mL | 16.13064 | 16.01506 | 0.11558 | 115.58 | 156.80 | 73.7 |
| TAINER | d | 1 | SLD | 4 mL | 7.32414 | 7.0855 | 0.23864 | 238.64 | 273.12 | 87.4 |
| RACK | e | 1 | GW5 | 5 mL | 14.14023 | 14.09346 | 0.04677 | 46.77 | 149.65 | 31.3 |

In this experiment, the amount of evaporation of the reagent was compared between when water is supplied to the liquid storing section 110 in the reagent storage 40 and when water is not supplied, and to what extent the amount of evaporation of the reagent reduced by supplying water to the liquid storing section was verified. The reagent containers used in the experiment were six reagent containers 300 each held in three alternately arranged second reagent container racks 320 of the six second reagent container racks 320 arranged on the second reagent table 22, and one reagent container 300 each held in all (five) first reagent container racks 310 arranged on the first reagent table 21. In table 1, the three second reagent container racks 320 used in the experiment is indicated as A to C, and the five first reagent container racks 310 are indicated as a to e. A plurality of types (GW15, Cup, IRC5, SLD, SIRC17, GW5, P-FDP) having different capacity and diameter of the upper opening was used for the reagent container 300. The RO water was used instead of the reagent, and only defined amount was accommodated in each reagent container 300. The reagent containers 300 were set in the reagent storage 40 in an equilibrium state of predetermined temperature and humidity, and the experiment was conducted. Table 1 describes the type of container and the capacity (liquid amount) in correspondence to each other.

The verification was carried out by comparing the amount of RO water evaporated within 24 hours for when water was supplied to the liquid storing section 110 (water supply) and when water was not supplied (not water supply). Specifically, the weight of the reagent container 300 at the start of experiment (0 hour) and the weight of the reagent container 300 after elapse of 24 hours were measured, the amount of evaporation of the RO water, or the difference in weights, was obtained, the amount of evaporation was converted to liquid amount (μL), and comparison was made for when water was supplied and for when water was not supplied. Table 1 describes the weight of the reagent container 300 at the start of the experiment (0 hour) and after elapse of 24 hours, the weight of the difference thereof, and the value in which the weight is converted to the liquid amount. For the case of no water supply, only the liquid amount of the RO water evaporated within 24 hours is described, and the description on the weight of the reagent container 300 at the start of the experiment (0 hour) and after elapse of 24 hours as well as the weight of the difference thereof are omitted.

As a result, the amount of evaporation when water is supplied to the liquid storing section 110 is about 21% to about 88%, and about 47% on average of when water is not supplied. In other words, the amount of evaporation of the reagent can be reduced to about half by supplying water to the liquid storing section 110, so that the evaporation of the reagent can be effectively suppressed.

The present invention is not limited to the above embodiments, and changes can be appropriately made within the scope of the invention defined by the Claims.

For instance, an example in which the present invention is applied to a blood coagulation analyzer has been described in the above embodiment, but the present invention may be applied to an immune analyzer and other biochemical analyzers.

In the above embodiment, the control unit 501 controls the liquid supply unit 118 to supply the cleaning solution (RO water) to the liquid storing section 110 every predetermined time and the cleaning solution that became redundant in the liquid storing section 110 is discharged by a constant-amount liquid discharge port 121 while the sample analyzer 1 is operating, but the present invention is not limited thereto. The control unit 501 may control the liquid supply unit 118 and the liquid discharge section 119 so that the cleaning solution in the liquid storing section 110 is discharged in a predetermined amount from all the liquid discharge ports 120 at the same time as when the cleaning solution is supplied to the liquid storing section 110 in a predetermined amount every predetermined time. The control unit 501 may control the liquid supply unit 118 and the liquid discharge section 119 so as to supply a predetermined amount of cleaning solution to the liquid storing section 110 after a predetermined amount of cleaning solution in the liquid storing section 110 is discharged from all the liquid discharge ports 120. The cleaning solution in the liquid storing section 110 can be changed even by such an operation.

The liquid to be stored in the liquid storing section 110 may be RO water containing antiseptic.

The liquid supply unit 118 supplies liquid from the cleaning solution tank 113 to the liquid storing section 110 through the supply piping 114 and the supply port 112, but the present invention is not limited thereto. Another supply port may be arranged in the heat transfer layer 78, another supply port and the cleaning solution tank 113 may be connected with another supply piping, the liquid supply unit 118 may supply the cleaning solution from the cleaning solution tank 113 to the upper surface of the heat transfer layer 78 through the other supply piping and the other supply port, and the cleaning solution may be stored at the upper surface of the heat transfer layer 78.

The flowing fan 88 generates air flow that flows from the upper side to the lower side, but may generate air flow that flows from the lower side to the upper side.

The temperature sensor for detecting the temperature in the reagent storage 40 is arranged in the reagent storage 40, and the control to change the rotation speed of the flowing fan 88 may be performed according to the temperature detected by the temperature sensor. For instance, if the temperature detected by the temperature sensor is higher than the target temperature, the control unit 501 may increase the rotation speed of the flowing fan 88. The cooling efficiency then can be enhanced. If the temperature detected by the instance sensor is lower than the target temperature, the control unit 501 may reduce the rotation speed of the flowing fan 88. Thus, occurrence of dew condensation in the reagent storage 40, and evaporation of the reagent can be suppressed.

What is claimed is:

1. A sample analyzer comprising:
    a reagent storage configured to store a reagent container containing a reagent used for analyzing a sample;
    a reagent arrangement section arranged within the reagent storage and comprising a first reagent table and a second reagent table;
    a heat transfer layer arranged at a bottom of the reagent storage;
    a cooler arranged below the heat transfer layer and out of the reagent storage, and configured to cool the heat transfer layer;
    a plurality of air blowers arranged within the reagent storage between the heat transfer layer and the first and second reagent tables, and configured to blow an air towards the heat transfer layer cooled by the cooler;
    a liquid storing section, which is arranged on an outer side of the heat transfer layer within the reagent storage, storing a liquid such that a surface of the liquid contacts an air within the reagent storage;
    a liquid supply unit configured to supply the liquid into the liquid storing section; and
    an analyzing unit configured to analyze a measurement sample prepared by mixing the sample and the reagent.

2. The sample analyzer of claim 1, wherein the reagent storage is substantially sealed.

3. The sample analyzer of claim 1, further comprising:
    a heater configured to warm the liquid to be stored in the liquid storing section, wherein
    the liquid supply unit supplies the liquid of higher temperature than a temperature of the air within the reagent storage into the liquid storing section.

4. The sample analyzer of claim 1, further comprising a liquid discharge unit configured to discharge the liquid stored in the liquid storing section to outside the reagent storage.

5. The sample analyzer of claim 4, wherein the liquid discharge unit comprises:
    a dam member formed to have a predetermined height; and
    a constant-amount liquid discharge port configured to discharge the liquid of an amount exceeding the dam member.

6. The sample analyzer of claim 5, further comprising a controller configured to control the liquid supply unit to supply the liquid into the liquid storing section.

7. The sample analyzer of claim 6, wherein the controller controls the liquid supply unit to supply the liquid into the liquid storing section every predetermined time.

8. The sample analyzer of claim 4, wherein the liquid discharge unit comprises an all liquid discharge port configured to discharge all the liquid stored in the liquid storing section.

9. The sample analyzer of claim 8, further comprising a controller configured to control the all liquid discharge port and the liquid supply unit to interchange the liquid in the liquid storing section.

10. The sample analyzer of claim 9, wherein the controller controls the all liquid discharge port and the liquid supply unit to interchange the liquid in the liquid storing section every predetermined time.

11. The sample analyzer of claim 8, further comprising a controller configured to control the all liquid discharge port to discharge the liquid stored in the liquid storing section responsive to an instruction from a user.

12. The sample analyzer of claim 11, wherein the instruction is an instruction to shut down the sample analyzer.

13. The sample analyzer of claim 1, wherein the liquid storing section is arranged around the heat transfer layer.

14. The sample analyzer of claim 1, wherein the air blower blows the air to a position different from a center portion of the heat transfer layer.

15. The sample analyzer of claim 1, wherein the heat transfer layer is arranged at an inner bottom surface of the reagent storage; and
the liquid storing section is formed by an outer side surface of the heat transfer layer, an inner bottom surface of the reagent storage excluding a region where the heat transfer layer is arranged, and an inner side surface of the reagent storage.

16. The sample analyzer of claim 1, further comprising an aspirating unit configured to aspirate the reagent contained in the reagent container stored within the reagent storage; and
a cleaner unit configured to clean the aspirating unit, wherein
the liquid supply unit supplies a cleaning solution used by the cleaner unit into the liquid storing section as the liquid.

17. A sample analyzer comprising:
    a reagent storage configured to store a reagent container containing a reagent used for analyzing a sample;
    a reagent arrangement section arranged within the reagent storage and comprising a first reagent table and a second reagent table;
    a heat transfer layer arranged at a bottom of the reagent storage;
    a cooler arranged below the heat transfer layer and out of the reagent storage, and configured to cool the heat transfer layer;
    a plurality of air blowers arranged within the reagent storage between the heat transfer layer and the first and second reagent tables, and configured to blow an air towards the heat transfer layer cooled by the cooler;
    a liquid storing section, which is arranged laterally around the heat transfer layer within the reagent storage, storing a liquid such that a surface of the liquid contacts an air within the reagent storage;
    a heat insulating member arranged between a lateral side of the heat transfer layer and the liquid storing section;
    a liquid supply unit configured to supply the liquid into the liquid storing section; and
    an analyzing unit configured to analyze a measurement sample prepared by mixing the sample and the reagent.

18. The sample analyzer of claim 17, wherein the air blowers are arranged farther from a top of the reagent storage than the reagent arrangement section.

* * * * *